US012577633B2

(12) United States Patent
Minoda

(10) Patent No.: US 12,577,633 B2
(45) **Date of Patent: *Mar. 17, 2026**

(54) AGENT FOR SELECTIVE METAL RECOVERY, METAL RECOVERY METHOD, AND METAL ELUTION METHOD

(71) Applicant: GALDIERIA CO., LTD., Tokyo (JP)

(72) Inventor: Ayumi Minoda, Tokyo (JP)

(73) Assignee: Galdieria Co., Ltd., Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 16/063,993

(22) PCT Filed: Dec. 22, 2016

(86) PCT No.: PCT/JP2016/088504

§ 371 (c)(1),
(2) Date: Jun. 19, 2018

(87) PCT Pub. No.: WO2017/111092

PCT Pub. Date: Jun. 29, 2017

(65) Prior Publication Data

US 2019/0024209 A1 Jan. 24, 2019

(30) Foreign Application Priority Data

Dec. 22, 2015 (JP) ................................ 2015-249567

(51) Int. Cl.
*C22B 3/18* (2006.01)
*B01J 20/22* (2006.01)
(Continued)

(52) U.S. Cl.
CPC ................ *C22B 3/18* (2013.01); *B01J 20/22* (2013.01); *B01J 20/24* (2013.01); *B01J 20/345* (2013.01);
(Continued)

(58) Field of Classification Search
CPC .. C12N 1/12; C22B 59/00; C22B 3/18; C22B 3/44; C22B 3/14; C22B 3/1666;
(Continued)

(56) References Cited

U.S. PATENT DOCUMENTS 4,908,317 A 3/1990 Wood et al.

FOREIGN PATENT DOCUMENTS

CN 105561922 * 5/2016
FR 3 001 961 A1 8/2014
(Continued)

OTHER PUBLICATIONS

What are Noble Metals Definition and List (Year: 2021) https://sciencenotes.org/noble-metals/.*
(Continued)

*Primary Examiner* — Tracy Vivlemore
*Assistant Examiner* — Lauren K Van Buren
(74) *Attorney, Agent, or Firm* — Morgan, Lewis & Bockius LLP

(57) ABSTRACT

The agent for selective metal recovery of the present invention includes a material derived from an alga belonging to the order Cyanidiales, which is dead cells or a cell surface layer of an alga belonging to the order Cyanidiales, or an artificial material produced by simulating the cell surface layer, or includes a porphyrin. The metal recovery method of the present invention includes an addition step of adding a material derived from an alga belonging to the order Cyanidiales, which is dead cells or a cell surface layer of an alga belonging to the order Cyanidiales, or an artificial material produced by simulating the cell surface layer, or adding a porphyrin, to a metal solution; and a recovery step of recovering a metal from the metal solution by the material derived from an alga belonging to the order Cyanidiales or the porphyrin.

8 Claims, 24 Drawing Sheets

FIG. 1 LEACHING AND RECOVERY OF METAL INTO CELLS FROM NEODYMIUM MAGNET
PHOTOAUTOTROPHY □ PHOTOMIXOTROPHY △ HETEROTROPHY SEMIANAEROBIC PHOTOAUTOTROPHY
X SEMIANAEROBIC HETEROTROPHY

(51) Int. Cl.

| | |
|---|---|
| ***B01J 20/24*** | (2006.01) |
| ***B01J 20/34*** | (2006.01) |
| ***B01J 45/00*** | (2006.01) |
| ***C02F 3/32*** | (2023.01) |
| ***C12N 1/12*** | (2006.01) |
| ***C22B 3/14*** | (2006.01) |
| ***C22B 3/16*** | (2006.01) |
| ***C22B 3/44*** | (2006.01) |
| ***C22B 7/00*** | (2006.01) |
| ***C22B 11/00*** | (2006.01) |
| ***C22B 59/00*** | (2006.01) |
| *C02F 101/20* | (2006.01) |

(52) U.S. Cl.

CPC ............... *B01J 45/00* (2013.01); *C02F 3/322* (2013.01); *C12N 1/12* (2013.01); *C22B 3/14* (2013.01); *C22B 3/1666* (2013.01); *C22B 3/44* (2013.01); *C22B 7/00* (2013.01); *C22B 11/00* (2013.01); *C22B 59/00* (2013.01); *B01J 2220/4843* (2013.01); *C02F 2101/20* (2013.01); *Y02P 10/20* (2015.11)

(58) Field of Classification Search

CPC . C22B 11/00; B01J 2220/4843; B01J 20/345; C02F 3/322

See application file for complete search history.

(56) References Cited

FOREIGN PATENT DOCUMENTS

| | | | | |
|---|---|---|---|---|
| JP | S60-162735 A | | 8/1985 | |
| JP | 2013-067826 A | | 4/2013 | |
| WO | WO 86/03480 A1 | | 6/1986 | |
| WO | WO2013042340 | * | 3/2013 | |
| WO | WO-2013042340 A1 | * | 3/2013 | .............. C02F 3/322 |

OTHER PUBLICATIONS

Minoda et al. "Recovery of rare earth elements from the sulfothermophile red algae *Galdieria sulphuraria* using aqueous acid" Appl Microbiol Biotechnology (2015) 99: 1513-1519, published online Oct. 7, 2014 (Year: 2014).*

Giovannetti et al. "Remarks on the reactions of a tetracarboxylic porphyrin with gold and silver ions: A spectrophotometric, TEM and SEM study." Polyhedron 27 (2008) 1047-1053 (Year: 2008).*

International Search Report mailed Feb. 7, 2017 in International Patent Application No. PCT/JP2016/088504, 1 page.

Giovannetti et al., "Reactions of anionic porphyrin with group 11 elements: a spectrophotometric and electrospray ionization mass spectrometry study", Talanta. Jul. 8, 2004; 63(4): 857-864. Epub Feb. 27, 2004.

Minoda et al., "Recovery of rare earth elements from the sulfothermophilic red alga *Galdieria sulphuraria* using aqueous acid", Appl Microbiol Biotechnol. Feb. 2015; 99(3): 1513-1519. Epub Oct. 7, 2014.

Extended European Search Report issued Jul. 8, 2019, in European Patent Application No. 16878978.2, 13 pages.

International Preliminary Report on Patentability issued Jun. 26, 2018 in International Patent Application No. PCT/JP2016/088504, 5 pages.

Cybulska, J. et al. Mechanical characteristics of artificial cell walls. J. Food Engineering 2010, 8 pages, 96(2), 287-294. https://www.sciencedirect.com/science/article/abs/pii/S0260877409003859.

Kuroda K., Ueda M. (2011) Yeast Biosorption and Recycling of Metal Ions by Cell Surface Engineering. In: Kotrba P., Mackova M., Macek T. (eds) Microbial Biosorption of Metals. Springer, Dordrecht. 13 pages, https://doi.org/10.1007/978-94-007-0443-5_10.

Li P.-S., Tao H.-C. Cell surface engineering of microorganisms towards adsorption of heavy metals. Critical Reviews in Microbiology 2015, 11 pages, 41(2), 140-149. https://doi.org/10.3109/1040841X.2013.813898.

Popper et al. "Plant and Algal Cell Walls: Diversity and Functionality", Annals of Botany, 114:1043-1048, 2014, doi: 10.1093/aob/mcu214, available online at www.aob.oxfordjournals.org.

Castenholz, R., "The Cyanidiales: Ecology, Biodiversity, and Biogeography", DOI: 10.1007/978-90-481-3795-4_19, Chapter Apr. 10, May 28, 2014, 13 pages.

Spadavecchia et al., "Tuning the shape and size of hybrid gold nanoparticles by porphyrins using seed-mediated synthesis", Chemical Physics Letters, 609:134-141, 2014, 8 pages.

EPO Communication pursuant to Article 94(3) EPC dated Feb. 17, 2022 for European Patent Application No. 16878978.2; 10 pages.

"Webelement Osmium", Dec. 16, 2016.

Office Action issued in U.S. Appl. No. 18/240,059 dated Nov. 13, 2025.

* cited by examiner

FIG. 1 LEACHING AND RECOVERY OF METAL INTO CELLS FROM NEODYMIUM MAGNET

PHOTOAUTOTROPHY PHOTOMIXOTROPHY HETEROTROPHY SEMIANAEROBIC PHOTOAUTOTROPHY

SEMIANAEROBIC HETEROTROPHY

AGENT FOR SELECTIVE METAL RECOVERY, METAL RECOVERY METHOD, AND METAL ELUTION METHOD

TECHNICAL FIELD

The present invention relates to an agent for selective metal recovery, a metal recovery method, and a metal elution method.

BACKGROUND ART

At present, since it is difficult to selectively recover 100 ppm or less of rare earth elements by utilizing a chemical exchange resin or the like, the rare earth elements are discarded as metal effluent. Regarding gold ions as well, several tens ppm or less of gold ions are not recyclable by the current chemical and engineering methods.

Thus, in recent years, metal recovery methods such as a method of eluting metals that are included as solids in a solution by utilizing living organisms (bioleaching), and a method of removing and adsorbing metal ions included in a solution by utilizing living organisms (biosorption), have been developed.

For example, Patent Literature 1 discloses a method of culturing red algae of the order Cyanidiales in a solution and eluting metal ions from metals included as solids in the solution, and a method of causing metal ions in a solution to adsorb to red algae and thereby recovering the metal ions.

Recovery of a metal by a living organism or a biosorbent is useful for metal recovery at low concentrations compared to chemical methods or engineering methods, and such metal recovery has been reported many times as an environment-friendly method enabling reduction of the amount of chemical agents at low cost.

CITATION LIST

Patent Literature

Patent Literature 1: Japanese Unexamined Patent Publication No. 2013-67826

SUMMARY OF INVENTION

Problems to be Solved by the Invention

However, recovery of metals by living organisms or biosorbents has a problem that selective recovery or purification of metals is difficult and practicalization has been impeded.

The present invention was achieved in view of the problems described above, and it is an object of the invention to provide an agent for selective metal recovery, a metal recovery method, and a metal elution method, which can be carried out with high efficiency at low cost compared to conventional methods.

Means for Solving the Problems

The gist of the present invention is as follows.

[1] An agent for selective metal recovery, the agent including a material derived from an alga belonging to the order Cyanidiales, which is dead cells or a cell surface layer of an alga belonging to the order Cyanidiales, or an artificial material produced by simulating the cell surface layer, or including a porphyrin. Meanwhile, living cells of an alga belonging to the order Cyanidiales may also be used as the material derived from an alga belonging to the order Cyanidiales. Furthermore, it is preferable that the porphyrin is a protonated porphyrin.

[2] The agent for selective metal recovery described in [1] described above, in which the porphyrin is coproporphyrin and/or pheophytin.

[3] The agent for selective metal recovery described in [1] or [2] described above, in which the porphyrin is a protonated compound.

[4] The agent for selective metal recovery described in any one of [1] to [3] described above, in which the agent selectively recovers a noble metal and/or a rare metal including a rare earth element.

[5] The agent for selective metal recovery described in any one of [1] to [4] described above, in which the agent selectively recovers a noble metal including gold or palladium, and/or a lanthanoid from a base metal mixture solution under acidic conditions.

[6] The agent for selective metal recovery described in [5] described above, in which the agent separates and selectively recovers a lanthanoid and iron based on the difference between the ionic radii of the respective elements and the degree of stability of complexes.

[7] The agent for selective metal recovery described in [1] described above, in which the cell surface layer of an alga belonging to the order Cyanidiales adsorbs a noble metal ion complex by an electrostatic interaction or ion exchange and desorbs the noble metal ion complex with a predetermined solution.

[8] The agent for selective metal recovery described in any one of [1] to [7] described above, in which the porphyrin forms nanoparticles by reducing a noble metal.

[9] A metal recovery method, including: an addition step of adding a material derived from an alga belonging to the order Cyanidiales, which is dead cells or a cell surface layer of an alga belonging to the order Cyanidiales, or an artificial material produced by simulating the cell surface layer, or adding a porphyrin, to a metal solution; and a recovery step of recovering a metal from the metal solution by the material derived from an alga belonging to the order Cyanidiales or the porphyrin.

[10] The metal production and recovery method described in [9] described above, in which the porphyrin is coproporphyrin and/or pheophytin.

[11] The metal recovery method described in [9] or [10] described above, in which the recovery step is a step of selectively recovering a noble metal and/or a rare metal including a rare earth element from the metal solution.

[12] The metal recovery method described in any one of [9] to [11] described above, in which the recovery step involves selective recovery of a noble metal including gold or palladium, and/or a lanthanoid from a base metal mixture solution under acidic conditions.

[13] The metal recovery method described in [12] described above, in which the recovery step involves separation and selective recovery of a lanthanoid and iron based on the difference between the ionic radii of the respective elements and the degree of stability of complexes.

[14] The metal recovery method described in any one of [9] to [13] described above, further including a reduction step of forming nanoparticles by causing the porphyrin to reduce a noble metal.

[15] The metal recovery method described in any one of [9] to [14] described above, in which the recovery step involves recovery of gold ions by adsorption using the material derived from an alga belonging to the order Cyanidiales, and the method includes a step of reducing gold ions by a reducing action of the porphyrin.

[16] A metal elution method for eluting a noble metal including gold or palladium, which has been recovered into a material derived from an alga belonging to the order Cyanidiales, which is dead cells or a cell surface layer of an alga belonging to the order Cyanidiales, or an artificial material produced by simulating the cell surface layer, the method including a step of adding a composition for metal elution, which is an acidic solution, to the material derived from an alga belonging to the order Cyanidiales.

[17] A metal elution method for eluting a metal which has been recovered into a material derived from an alga belonging to the order Cyanidiales, which is dead cells or a cell surface layer of an alga belonging to the order Cyanidiales, or an artificial material produced by simulating the cell surface layer, the method including a step of adding a composition for metal elution including a mixed liquid of ammonia and an ammonium salt to the material derived from an alga belonging to the order Cyanidiales.

Furthermore, in regard to the metal recovery method of the present invention, it is preferable that gold ions are recovered and converted to gold nanoparticles by reduction in a short time period, by combining (1) recovery by adsorption utilizing a cell surface layer of an alga belonging to the order Cyanidiales, and (2) reduction of gold ions by a porphyrin, and thereby the purity is increased.

Furthermore, in regard to the metal recovery method of the present invention, it is preferable that a noble metal complex is eluted with a purity of 99.98%, by performing desorption by a particular solution after the (1) recovery by adsorption utilizing a cell surface layer of an alga belonging to the order Cyanidiales.

Furthermore, in regard to the metal recovery method of the present invention, it is preferable that only noble metal ions are purified by burning after the (1) recovery by adsorption utilizing a cell surface layer of an alga belonging to the order Cyanidiales.

In addition, regarding the desorption, a noble metal may be extracted and purified as a complex, by utilizing a mixed liquid of aqueous ammonia and an ammonium salt (ammonium chloride, ammonium sulfate, ammonium carbonate, ammonium bromide, or the like). It is effective for a cell surface layer of an alga belonging to the order Cyanidiales; however, it can also be used with existing ion exchange resins and the like. Meanwhile, it is insufficient with aqueous ammonia only.

That is, regarding the metal recovery method of the present invention, it is preferable to use a mixed liquid of ammonia and an ammonium salt as a solution for eluting a metal which has been recovered into a material derived from an alga belonging to the order Cyanidiales, which is dead cells or a cell surface layer of an alga belonging to the order Cyanidiales, or an artificial material produced by simulating the cell surface layer.

Effects of the Invention

According to the present invention, provided is an effect that an agent for selective metal recovery, a metal recovery method, and a metal elution method, by which selective recovery, elution, purification, and the like of a metal can be carried out efficiently at low cost, can be provided.

EMBODIMENTS FOR CARRYING OUT THE INVENTION

Figure 1:
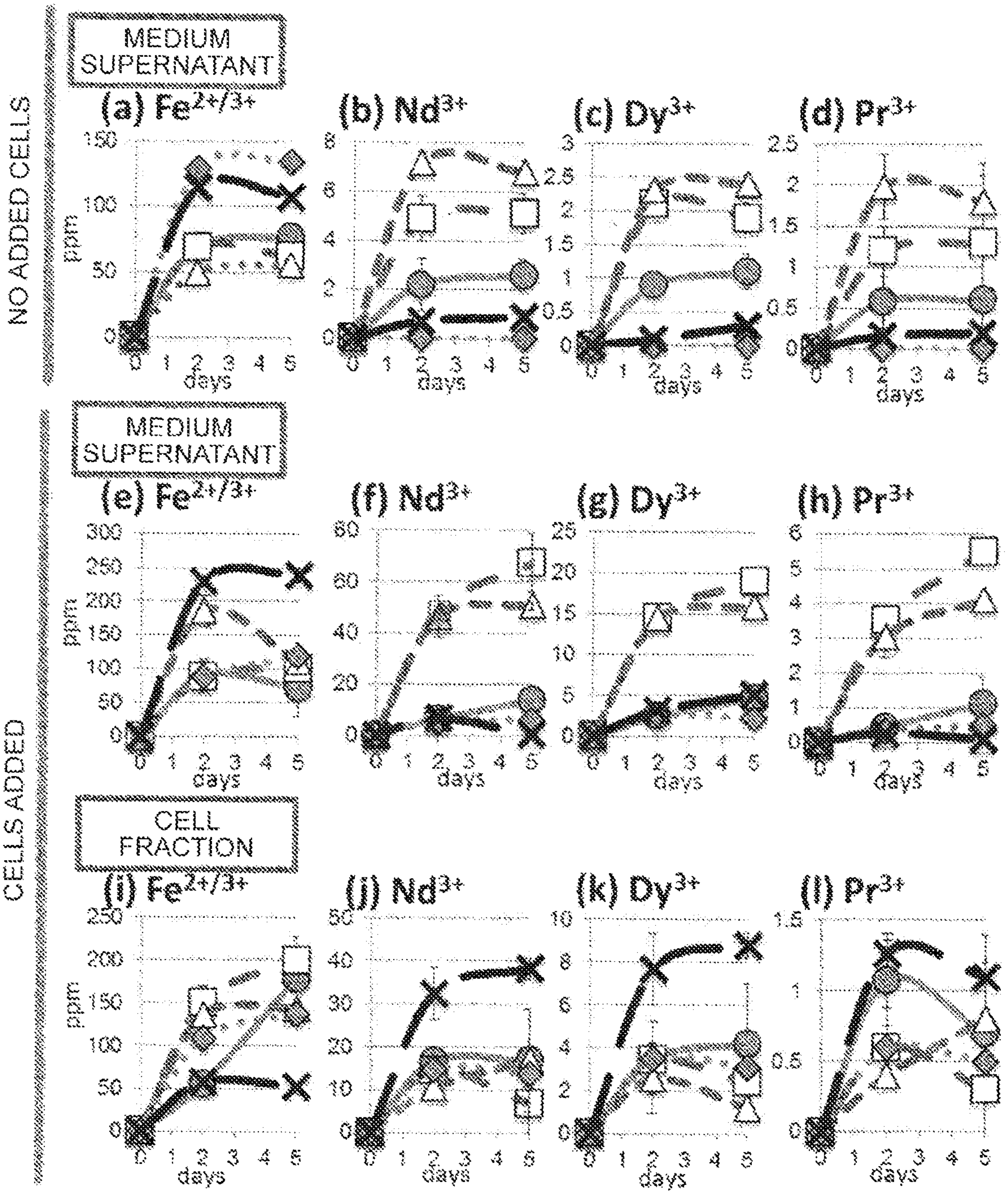
FIG. 1 is a diagram of graphs showing the ICP-MS measurement results of the concentrations of various metals included in a culture fluid supernatant and cell fractions at the time of non-addition/addition of cells.

Hereinafter, the agent for selective metal recovery, metal recovery method, and metal elution method of the present invention will be described in detail. First, the present embodiments will be described together with the background from which the present invention was devised, and subsequently, Examples accompanied by experimental results will be described. In addition, this invention is not intended to be limited by the following present embodiments and Examples. For example, in the following embodiments and Examples, algal bodies of red algae belonging to the order Cyanidiales, or a cell surface layer, an algal body adsorbent, and cell surface layer fractions of red algae may be described; however, the present invention is not intended to be limited to these, and the present invention may also be applied to materials derived from algae belonging to the order Cyanidiales, such as dead cells and a cell surface layer of an alga belonging to the order Cyanidiales, and an artificial material produced by simulating the cell surface layer.

EMBODIMENTS

An overview of the agent for selective metal recovery, the metal recovery method, and the metal elution method according to the present embodiments will be described. As described above, recovery of a metal by a living organism or a biosorbent is a method that is useful for recovery of a metal at a low concentration or imposes less environmental burden by enabling reduction of the amount of chemical agents at low cost compared to a chemical method or an engineering method; however, selective recovery or purification of metals is difficult, and practicalization has been impeded. Therefore, recovery of several tens ppm or less of noble metal ions by any one of a chemical method, an engineering method, and a biological method is difficult, and noble metal ions are discarded as metal effluent.

Thus, the inventor of the present invention conducted a thorough investigation, and as a result, the inventor found that red alga of *Galdieria sulphuraria* (hereinafter, referred to as "*G. sulphuraria*") belonging to the order Cyanidiales performs elution or recovery into cells of rare earth elements from neodymium magnet waste materials depending on the culture conditions. Furthermore, the inventor of the present invention discovered that selectivity between rare earth elements and iron is exhibited in the elution or recovery thereof (see Example 1 described below).

The incubation time after cells of *G. sulphuraria* are added to a metal solution containing neodymium magnet waste materials and the like is not particularly limited; however, the incubation time is preferably 1 minute to 24 hours, and more preferably 10 minutes to 30 minutes. Furthermore, the incubation temperature is not particularly limited; however, the incubation temperature is preferably 0° C. to 70° C. When incubation is performed under the above-described conditions of incubation time and/or incubation temperature, the efficiency for elution or recovery into cells of rare earth elements tends to increase.

Next, the inventor of the present invention identified coproporphyrin as a chelator in relation to the elution of rare earth elements (see Example 2 described below). Furthermore, the inventor of the present invention found that coproporphyrin chelates rare earth elements or divalent iron, while not chelating trivalent iron.

Since iron exists in a trivalent form under acidic conditions, the inventor of the present invention found that only those rare earth elements can be selectively chelated, even in the presence of iron, using protonated coproporphyrin by leaving the compound under acidic conditions. That is, the inventor discovered that this is an important mechanism by which selectivity between rare earth elements and iron in red algae such as *G. sulphuraria* is exhibited.

That is, according to an embodiment of the present invention based on this discovery, a noble metal such as gold or palladium, or a rare earth element such as a lanthanoid is selectively recovered from a base metal mixture solution of iron and the like, by using a porphyrin such as coproporphyrin and leaving the compound under acidic conditions. As such, when a porphyrin such as coproporphyrin is utilized under acidic conditions, even in a case in which base metals such as iron exist in large quantities, noble metals or rare earth elements can be selectively recovered from metal effluent. Furthermore, regarding the reason why trivalent iron is not chelated but trivalent rare earth elements are chelated, the differences in the ionic radius and the degree of stability of complexes may be considered as the causative factors. Therefore, even between rare earth elements that have very similar properties and are currently not easily separable industrially (for example, Dy and Tb), separation can be achieved based on the difference in the ionic radius or the difference in the degree of stability of complexes.

Furthermore, the inventor of the present invention found that in the phenomenon in which red alga *G. sulphuraria* reduces gold ions in the presence of light and thereby forms nanoparticles (Example 7 described below), a porphyrin such as coproporphyrin or pheophytin accelerates reduction of gold. Here, the inventor found that coproporphyrin forms gold particles of larger sizes, compared to pheophytin, which is a kind of the same porphyrin (Example 8 described below).

That is, according to an embodiment of the present invention based on this discovery, gold particles are formed by reducing gold ions in a solution by using a porphyrin such as coproporphyrin or pheophytin. In addition, based on the same principle, according to an embodiment of the present invention, a solid metal may also be formed by using a porphyrin and reducing a metal having a high oxidation-reduction potential, such as a noble metal ion, in a solution.

As described above, as a result of thorough investigation of the inventor of the present invention, the inventor finally devised an invention, by which: (1) a porphyrin works as a chelator to selectively adsorb (chelate) metal ions of a noble metal or a rare earth element; (2) a metal complex of a noble metal, a rare earth element, or the like can be selectively adsorbed from a base metal mixture solution of iron and the like by leaving the solution on a cell surface layer of an alga belonging to the order Cyanidiales under acidic conditions; and (3) noble metal ions are reduced and converted to solid particles by using a porphyrin.

A porphyrin is a compound existing in all living organisms including from microorganisms to human beings, and in recent years, chemical synthesis methods have also been developed. By utilizing a porphyrin derived from a living organism or chemical synthesis, an inexpensive, highly efficient method compared to conventional methods can be provided in connection with selective recovery of rare earth elements at low concentrations, which are currently not recycled, or nanoparticle formation or recovery based on reduction of gold ions.

[Embodiments of Composition for Metal Elution/Metal Elution Method]

An overview of the composition for metal elution/metal elution method of the present embodiments will be described. As described above, recovery of a metal by a living organism or a biosorbent is a method that is useful for recovery of a metal at a low concentration or imposes less environmental burden by enabling reduction of the amount of chemical agents at low cost compared to a chemical method or an engineering method; however, selective recovery or purification of metals is difficult, and practicalization has been impeded. Therefore, recovery of several tens ppm or less of noble metal ions by any one of a chemical method, an engineering method, and a biological method is difficult, and noble metal ions are discarded as metal effluent.

Conventionally, as a method for purifying a noble metal collected by an alga or a microorganism, methods of using elution by a mixed solution of thiourea (thiourea) and hydrochloric acid, which is utilized for leaching from minerals, or using combustion have been disclosed. Since elution methods using thiourea are disadvantageous from the viewpoints of economic efficiency and environment, and also it is difficult to apply the elution methods to subsequent chemical processes, practicalization has not been achieved. Furthermore, also for combustion methods, being disadvantageous from the viewpoints of economic efficiency and environment has been a problem.

The inventor of the present invention conducted a thorough investigation, and as a result, the inventor discovered that algae belonging to the order Cyanidiales recover noble metals at low concentrations with high efficiency (see Examples 3 and 4 described below). Base on this discovery, the inventor of the present invention has devised a method of selectively recovering noble metals into algal cells by utilizing an alga belonging to the order Cyanidiales by adjusting the acid concentration of a metal effluent (aqua regia solution) including gold and palladium to about 0.5 M (see Example 5 described below), and extracting and purifying only noble metals from a material derived from an alga belonging to the order Cyanidiales, which is dead cells or a cell surface layer of an alga belonging to the order Cyanidiales, or an artificial material produced by simulating the cell surface layer (see Example 6 described below).

An embodiment of the present invention based on these findings is to provide a composition for metal elution, which is an acidic solution, for eluting a noble metal such as gold or palladium which has been recovered into a material derived from an alga belonging to the order Cyanidiales, such as an algal body adsorbent such as an algal body of a red alga or a cell surface layer of a red alga. In other words, an embodiment of the present invention relates to a metal elution method of eluting a noble metal such as gold or palladium which has been recovered into a material derived from an alga belonging to the order Cyanidiales, the method including a step of adding a composition for metal elution, which is an acidic solution, to an algal body of a red alga or an algal body adsorbent. The composition for metal elution is not particularly limited; however, from the viewpoint of increasing the efficiency of elution, it is preferable to use an acidic solution including aqua regia. Furthermore, the acid concentration of the acidic solution is not particularly limited; however, from the viewpoint of increasing the efficiency of elution, the acid concentration is preferably 0.1 M to 10 M, more preferably 0.1 M to 1.0 M, and particularly preferably 0.3 M to 0.8 M. Furthermore, an embodiment of the present invention includes a step of adding a composition for metal elution including a mixed liquid of ammonia and an ammonium salt, which is intended for eluting a metal which has been recovered into a material derived from an alga belonging to the order Cyanidiales, to an algal body of a red alga or an algal body adsorbent (see Example 6 described below).

Thereby, the noble metal ions adsorbed to the material derived from an alga belonging to the order Cyanidiales, including an algal body of a red alga, dead cells of a red alga, and the like, can be eluted with high purity, and methods such as bioleaching and biosorption can be further improved. Therefore, the present invention can contribute to recovery and purification of noble metals with high efficiency at low cost compared to conventional methods, by using red algae.

EXAMPLES

Subsequently, in order to demonstrate the agent for selective metal recovery, the composition for metal elution, the metal production method, and the metal elution method according to the embodiments of the present invention, Example 1 to Example 9 carried out by the inventors of the present invention will be described.

Example 1

Example 1 relating to the elution (bioleaching) and recovery into cells (biosorption) of rare earth elements from a neodymium magnet waste material will be described.

Method

First, a neodymium magnet waste material containing iron as a main component [4.7 g of $Fe^{2+/3+}$, 1.7 g of $Nd^{3+}$, 0.5 g of praseodymium ($Pr^{3+}$), and 0.4 g of $Dy^{3+}$ (see the following table) in 10 g] was added to 20 ml of a *G. sulphuraria* culture fluid. More specifically, regarding the culture conditions, the cell density in 10 mg of neodymium magnet waste material/20 ml of 2× Allen's medium was adjusted to $10^8$ cells/ml.

TABLE 1

| | | |
|---|---|---|
| Fe | 4.7 | [235 ppm*] |
| Nd | 1.7 | [85 ppm*] |
| Pr | 0.5 | [25 ppm*] |
| Dy | 0.4 | [20 ppm*] |
| Others (Tb, B, Co, C, Al) | 0.2 | |
| $H_2O$ | 2.5 | [* Concentrations in the case of being totally dissolved in] |
| Total | 10 g | 20 ml |

Subsequently, red alga *G. sulphuraria* was cultured for five days under the following five different culture conditions.

(1) Photoautotrophic conditions (Light) in which cells proliferate only by photosynthesis.
(2) Photomixotrophic conditions (Light+Glc) in which both photosynthesis and metabolism of organic materials are carried out.
(3) Heterotrophic conditions (Dark+Glc) in which only organic materials are metabolized in the dark.
(4) Semianaerobic autotrophic conditions (Light) in which cells proliferate by photosynthesis under semianaerobic conditions attained by implementing forced ventilation with 100% carbon dioxide.
(5) Semianaerobic heterotrophic conditions (Dark+Acetate) in which fermentation is carried out in the dark under semianaerobic conditions attained by implementing forced ventilation with 100% nitrogen.

Then, the concentrations of the various metals included in the culture fluid supernatants and cell fractions were determined by ICP-MS on Day 0, Day 2, and Day 5 of culture.

Results

FIG. 1 is a diagram of graphs showing the ICP-MS results for the concentrations of the various metals included in the culture fluid supernatants and cell fractions at the time of non-addition/addition of cells. As shown in FIG. 1, in a case in which only a neodymium magnet waste material was added to the culture fluid, and cells were not added, iron was eluted into the culture fluid; however, rare earth elements ($Nd^{3+}$, $Dy^{3+}$, and $Pr^{3+}$) hardly dissolved in the medium (FIG. 1, a to d).

In contrast, in a case in which *G. sulphuraria* cells were added to the culture fluid together with a neodymium magnet waste material, the concentrations of the rare earth elements in the culture fluid supernatants increased under the (2) photomixotrophic conditions and the (3) heterotrophic conditions (FIG. 1, f to h). The concentrations of iron in the culture fluid supernatants under the (2) photomixotrophic conditions and the (3) heterotrophic conditions were not different from the concentrations obtained without addition of cells, and the conditions in which the concentration of iron in the culture fluid supernatant was the highest were the (5) semianaerobic heterotrophic conditions (FIG. 1, e).

Next, when the metal concentrations in the cell fractions in a case in which a neodymium magnet waste material and cells were added to the culture fluid were examined, the concentrations of the rare earth elements were the highest under the (5) semianaerobic heterotrophic conditions (FIG. 1, j to l). In contrast, the concentration of iron in the cell fraction under these (5) semianaerobic heterotrophic conditions was the lowest among the five culture conditions (FIG. 1, i).

SUMMARY

<1> It was found that when cells of *G. sulphuraria* are added to the medium, elution of iron and rare earth elements occurs more efficiently in the culture fluid supernatant. <2> It was found that the concentrations of iron and rare earth elements in the culture fluid supernatant or the cell fraction vary depending on the culture conditions for *G. sulphuraria*. <3> It was found that not only the elution of rare earth elements from a neodymium magnet waste material into the medium supernatant but also concentration of rare earth elements into the cell fraction occur under semianaerobic conditions.

DISCUSSION

Conventionally, in a bioleaching process utilizing microorganisms, a step of recovering metals from the solution after a step of eluting metals from a metal waste material or mineral ore (bioleaching) is needed. However, findings were obtained that when *G. sulphuraria* is utilized, not only rare earth elements can be eluted into a medium-dissolved culture fluid supernatant, but also the rare earth elements can be recovered into cells, and thus, two steps of elution and recovery in conventional cases can be combined into one step.

Example 2

Example 2 relating to the identification of a chelator exhibiting selectivity for rare earth elements will be described below.

Figure 2:
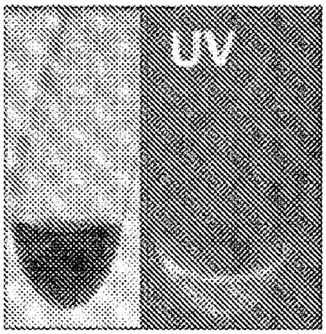
FIG. 2 is a diagram (photograph as a substitute for a diagram) showing a visible light image and a UV irradiation image of a fraction including ethyl acetate in a medium supernatant (ethyl acetate-extracted fraction obtained by mixing a medium supernatant and ethyl acetate).
Figure 3:
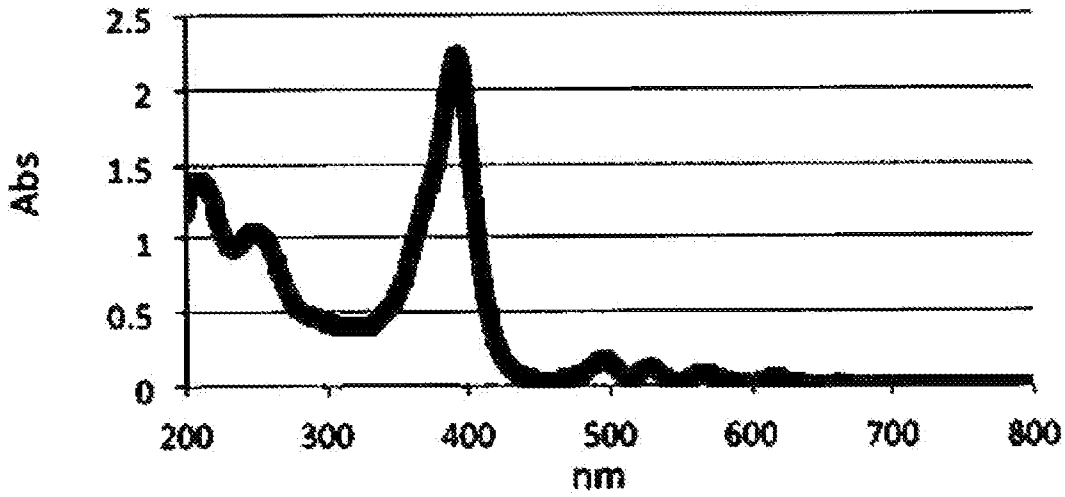
FIG. 3 is a diagram of a graph showing the absorption wavelength on the horizontal axis and the light absorbance on the vertical axis for a fraction including ethyl acetate in a medium supernatant (ethyl acetate-extracted fraction obtained by mixing a medium supernatant and ethyl acetate).

From the results of Example 1, it was predicted that the medium supernatant obtained under the (2) photomixotrophic conditions includes a chelator exhibiting high affinity for rare earth elements, compared to iron. Thus, a fraction including ethyl acetate was fractionated from the medium supernatant, and the optical characteristics were investigated. FIG. 2 is a diagram (photograph as a substitute for a diagram) showing a visible light image and a UV irradiation image of a fraction including ethyl acetate in a medium supernatant (ethyl acetate-extracted fraction obtained by mixing a medium supernatant and ethyl acetate). FIG. 3 is a diagram of graphs showing the absorption wavelength on the horizontal axis and the light absorbance on the vertical axis for a fraction including ethyl acetate in a medium supernatant (ethyl acetate-extracted fraction obtained by mixing a medium supernatant and ethyl acetate).

Figure 4:
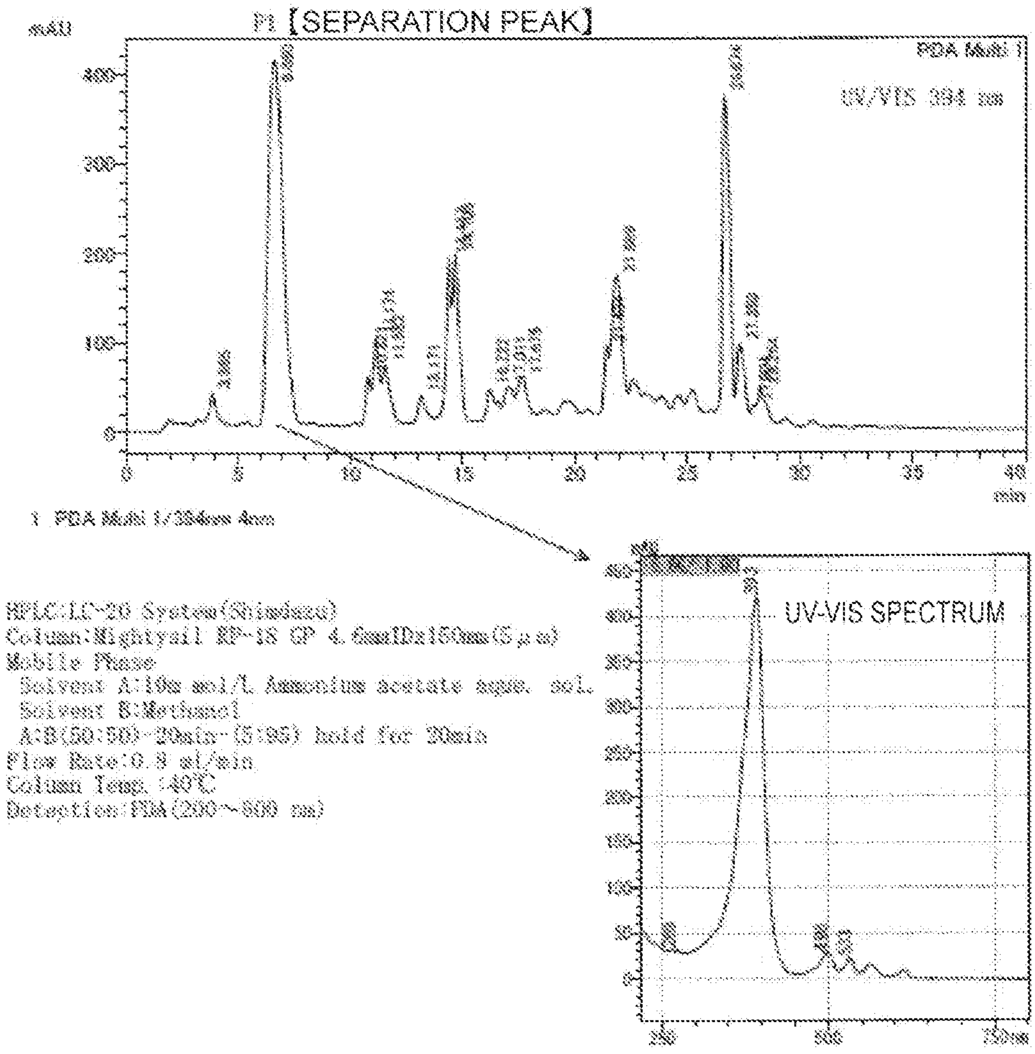
FIG. 4 is a diagram showing an ultraviolet-visible light absorption spectrum obtained before HPLC purification.

As a result, as shown in FIG. 2 and FIG. 3, a colorant having an absorption maximum at 400 nm and rare earth elements were included in large quantities. Furthermore, purification by HPLC was carried out based on the absorption maximum at 400 nm. Here, FIG. 4 is a diagram showing an ultraviolet-visible light absorption spectrum obtained before HPLC purification, and FIG. 5 is a diagram showing an ultraviolet-visible light absorption spectrum obtained after HPLC purification.

Figure 5:
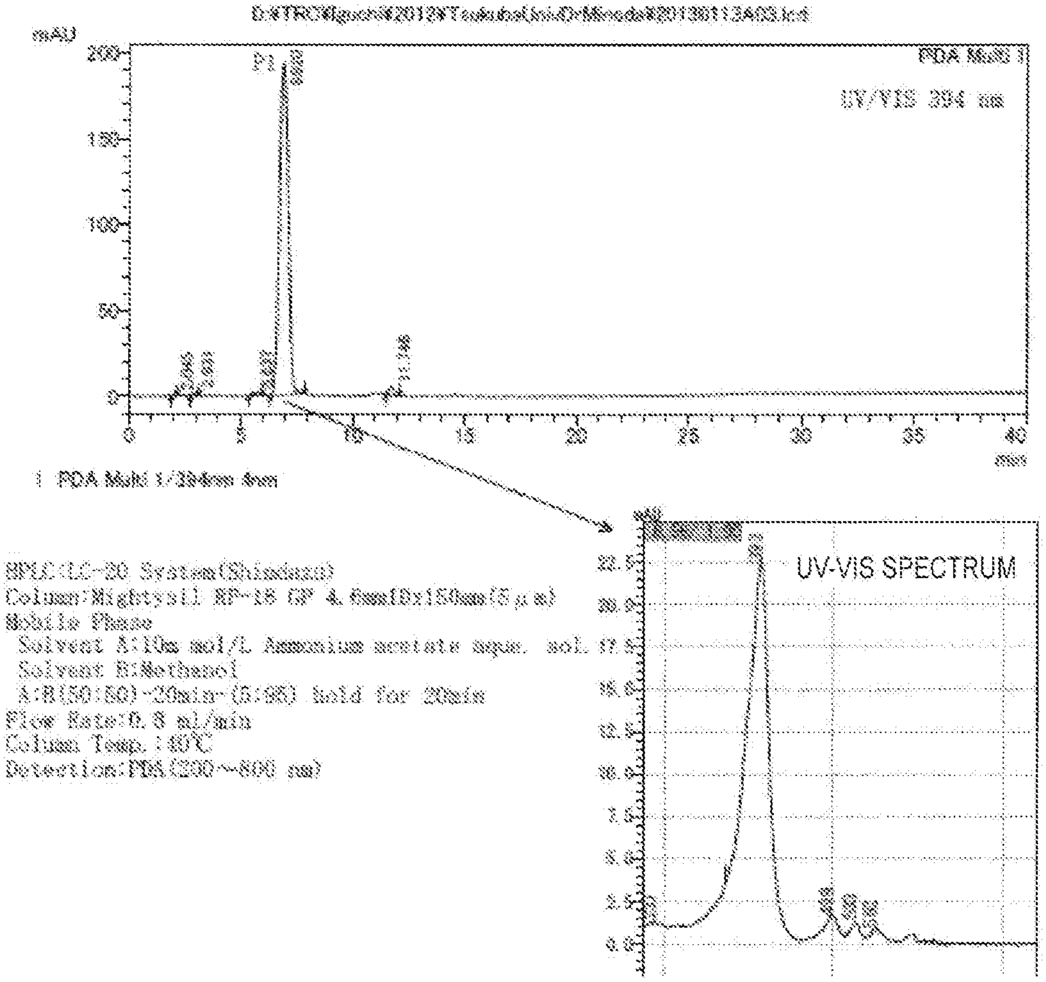
FIG. 5 is a diagram showing an ultraviolet-visible light absorption spectrum obtained after HPLC purification.

Then, an MS/MS analysis and a 1H-NMR analysis of the colorant purified by HPLC as shown in FIG. 5 were performed. Here, FIG. 6 is a diagram showing the MS/MS analysis results for the colorant purified by HPLC, and FIG. 7 is a diagram showing the 1H-NMR analysis results for the colorant purified by HPLC.

Figure 6:
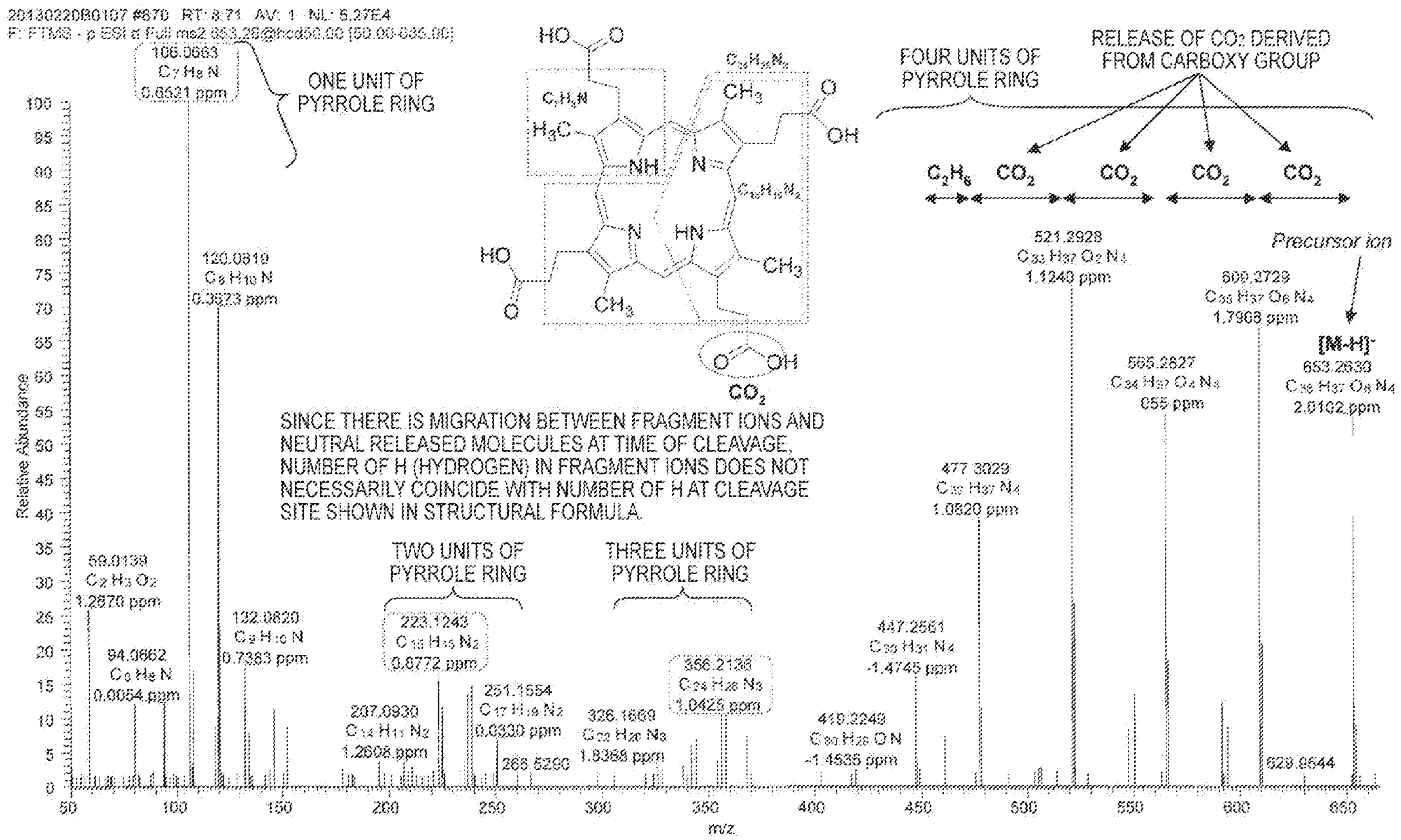
FIG. 6 is a diagram showing the MS/MS analysis results for a colorant purified by HPLC.
Figure 7:
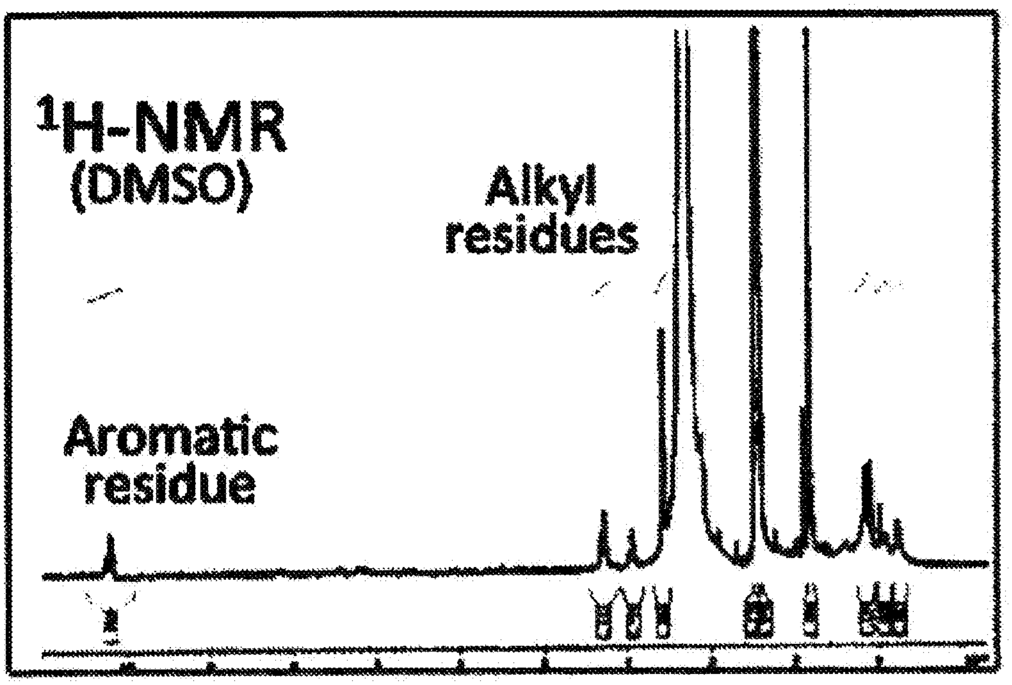
FIG. 7 is a diagram showing the 1H-NMR analysis results for a colorant purified by HPLC.

As shown in FIG. 6 and FIG. 7, as a result of performing the MS/MS analysis and 1H-NMR analysis, it was found that the colorant purified by HPLC was coproporphyrin (chemical structure thereof is shown below).

[Chemical Formula 1]

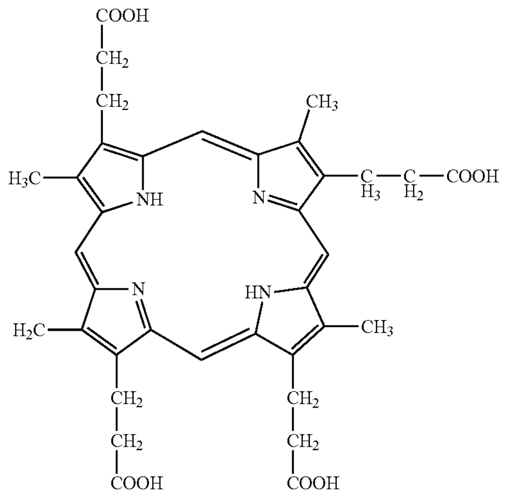

Figure 8:
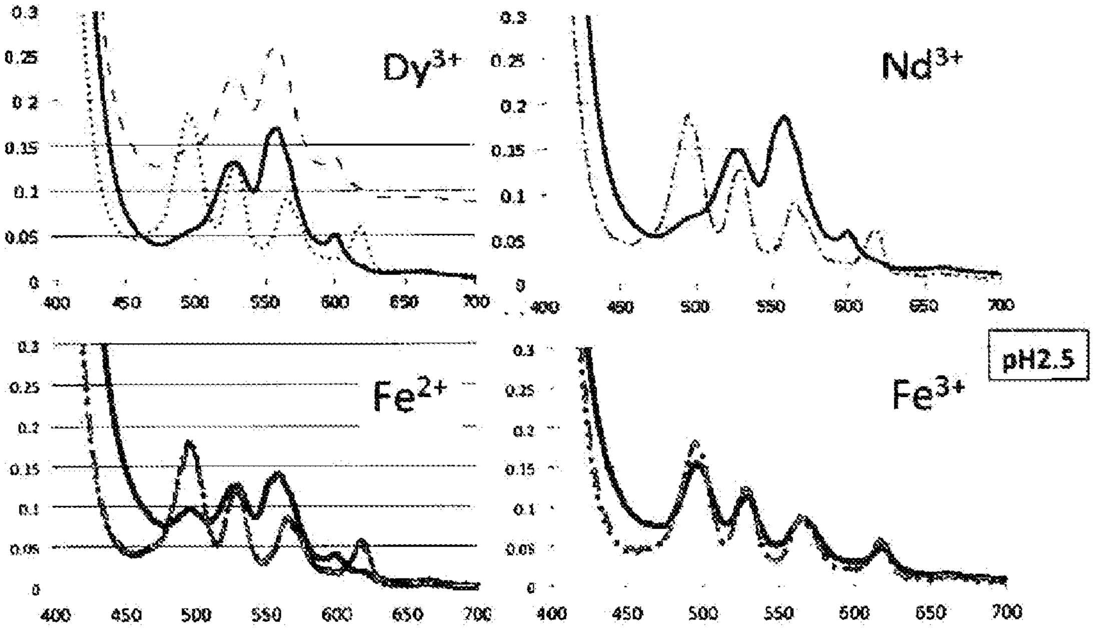
FIG. 8 is a diagram showing the spectra obtained at the time of no metal addition (HPLC purification product (coproporphyrin) of an ethyl acetate-extracted fraction: dotted lines in the diagram), at the time of metal addition of $Nd^{3+}$, $Dy^{3+}$, $Fe^{2+}$, and $Fe^{3+}$ (HPLC purification product (coproporphyrin) of an ethyl acetate-extracted fraction+metals: solid lines in the diagram), and at the time of EDTA addition (HPLC purification product (coproporphyrin) of an ethyl acetate-extracted fraction+metals+EDTA: broken lines in the diagram).

Generally, it is well known that a spectral shift in the visible light region occurs when a metal is chelated. Thus, $Nd^{3+}$, $Dy^{3+}$, $Fe^{2+}$, and $Fe^{3+}$ were added to a purified colorant, and any changes in the spectrum of the visible light region were observed. FIG. 8 is a diagram showing the spectra obtained at the time of no metal addition (HPLC purification product (coproporphyrin) of an ethyl acetate-extracted fraction: dotted lines in the diagram), at the time of metal addition of $Nd^{3+}$, $Dy^{3+}$, $Fe^{2+}$, and $Fe^{3+}$ (HPLC purification product (coproporphyrin of an ethyl acetate-extracted fraction+metals: solid lines in the diagram), and at the time of further addition of EDTA (HPLC purification product (coproporphyrin) of an ethyl acetate-extracted fraction+metals+EDTA: broken lines in the diagram).

As a result, as shown in FIG. 8, a shift in the spectrum of the visible light region was seen only with $Nd^{3+}$, $Dy^{3+}$, and $Fe^{2+}$, and a shift was not observed with $Fe^{3+}$. Furthermore, when EDTA as a metal chelator was added, the spectral shifts observed with $Nd^{3+}$ and $Fe^{2+}$ returned to the state before the addition of the metals, while the spectral shift observed with $Dy^{3+}$ did not return to the original state.

Based on these results, it was confirmed that $Nd^{3+}$ and $Fe^{2+}$ were chelated by coproporphyrin. It was found that the bonding state of $Dy^{3+}$ and coproporphyrin was not inhibited by the addition of EDTA, unlike the chelated state of $Nd^{3+}$ and $Fe^{3+}$, and a structural change in the porphyrin ring occurred as a result of the addition of EDTA. These results are considered to be caused by the difference in the stability constant of an EDTA complex between the various rare earth elements.

The experiment of bioleaching of Example 1 was carried out under acidic (pH 2.5) conditions. Since iron exists not in a divalent form ($Fe^{2+}$) but in a trivalent form ($Fe^{3+}$) under acidic conditions, it is speculated that coproporphyrin in the medium supernatant chelates more rare earth elements ($Nd^{3+}$ and $Dy^{3+}$) than iron ($Fe^{3+}$).

From the results described above, the inventors of the present invention found that rare earth elements and iron can be separated by utilizing coproporphyrin under acidic conditions in which iron exists in a trivalent form. That is, the inventors found a method of selectively recovering rare earth elements such as lanthanoids or noble metals from a base metal mixture solution of iron and the like, under acidic conditions by using a porphyrin.

Example 3

Figure 9:
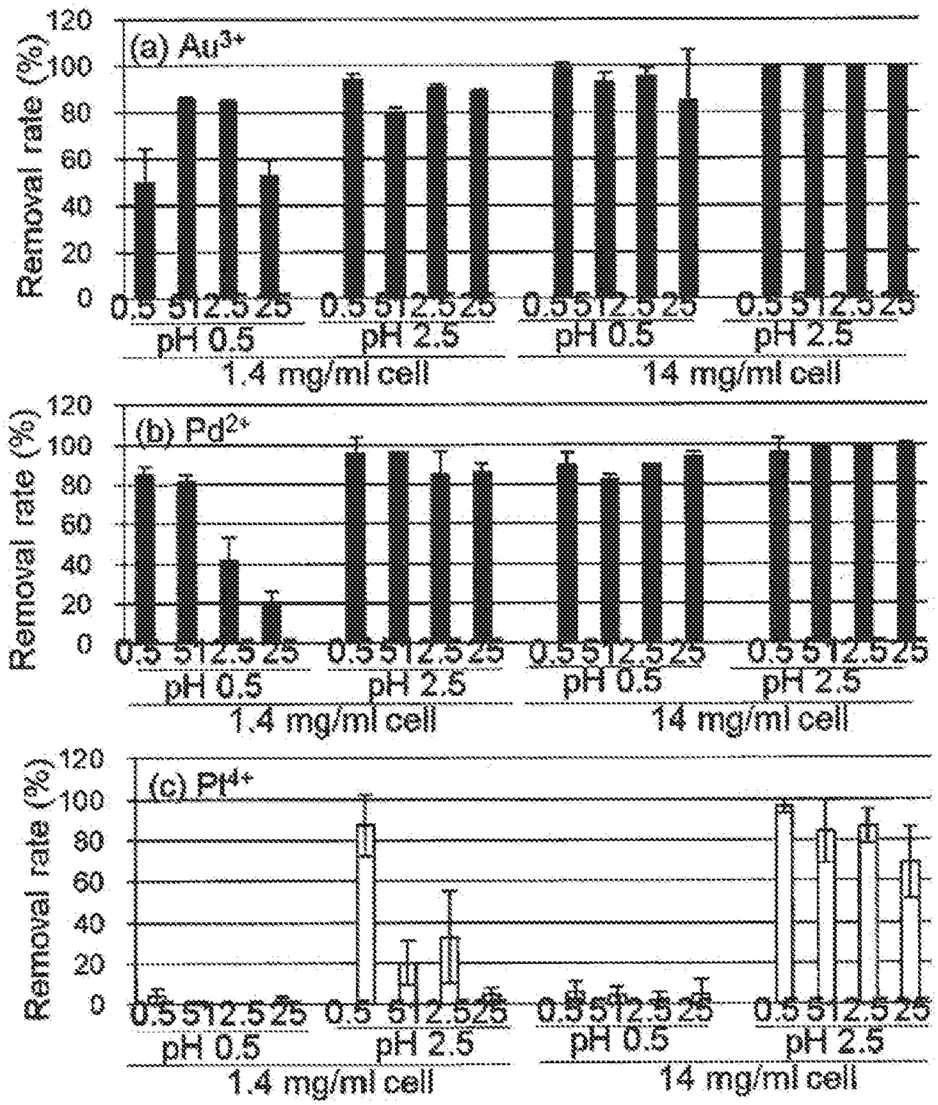
FIG. 9 is a diagram of graphs showing the recovery efficiencies for gold, platinum, and palladium achieved by *G. sulphuraria.*

Example 3 relating to the recovery of noble metals by an alga belonging to the order Cyanidiales will be described below. In Example 3, the cell concentration and the acid concentration of a hydrochloric acid solution were changed, and then the recovery efficiencies for 0 to 25 ppm of gold, platinum, and palladium achieved by *G. sulphuraria* were investigated. FIG. 9 is a diagram of graphs showing the recovery efficiencies for gold, platinum, and palladium achieved by *G. sulphuraria.*

Regarding the acid concentration, the experiment was carried out using two kinds of solutions, namely, a 0.4 M hydrochloric acid solution (pH 0.5) and a 40 mM hydrochloric acid solution (pH 2.5). To these hydrochloric acid solutions, $Au^{3+}$, $Pd^{2+}$, and $Pt^{4+}$ were added, and *G. sulphuraria* cells were cultured therein for 30 minutes. Regarding the cell density, the experiment was carried out with two kinds of densities, namely, 1.4 mg/ml and 14 mg/ml as dry weights.

After culturing, supernatant fractions and cells were separated by centrifugation. The metal concentrations in the supernatant fraction were determined by ICP-MS, and the percentage of each fraction was determined by subtracting the concentration obtainable as a control in the case of culturing without addition of cells from the concentration in each fraction. In addition, the concentrations of the hydrochloric acid solutions including $Au^{3+}$, $Pd^{2+}$, and $Pt^{4+}$ without cell addition were as follows.

0.5±0.2, 4.5±0.9, 14±1.4, 28±2.8 ($Au^{3+}$, pH0.5)
0.9±0.3, 2.9±0.1, 7.6±0.8, 16±3.6 ($Au^{3+}$, pH2.5)
0.4±0.1, 4.1±1.2, 8.4±1.6, 20±3.3 ($Pd^{2+}$, pH0.5)
0.3±0.1, 4.0±0.7, 9.4±2.0, 17±1.0 ($Pd^{2+}$, pH2.5)
0.6±0.1, 6.0±1.5, 15±3.2, 31±5.1 ($Pt^{4+}$, pH0.5)
0.6±0.4, 3.4±1.5, 8.6±2.0, 19±4.1 ($Pt^{4+}$, pH2.5)
(each value is the average value of three independent experiment values for each solution±SD value)

As a result, as shown in FIG. 9, it was found that gold and palladium are recovered into cells with the highest efficiencies at pH 0.5 (0.4 M HCl). Furthermore, it was found that platinum is recovered into cells with high efficiency by increasing the amount of cells at a low acid concentration. Therefore, it was confirmed that noble metals at very low concentrations can be recovered with high efficiency by utilizing red algae such as the algae belonging to the order Cyanidiales.

Example 4

Example 4 relating to the recovery efficiency in living cells (Living Cells) and dead cells (Freeze-thawed Cells) will be described below.

Figure 10:
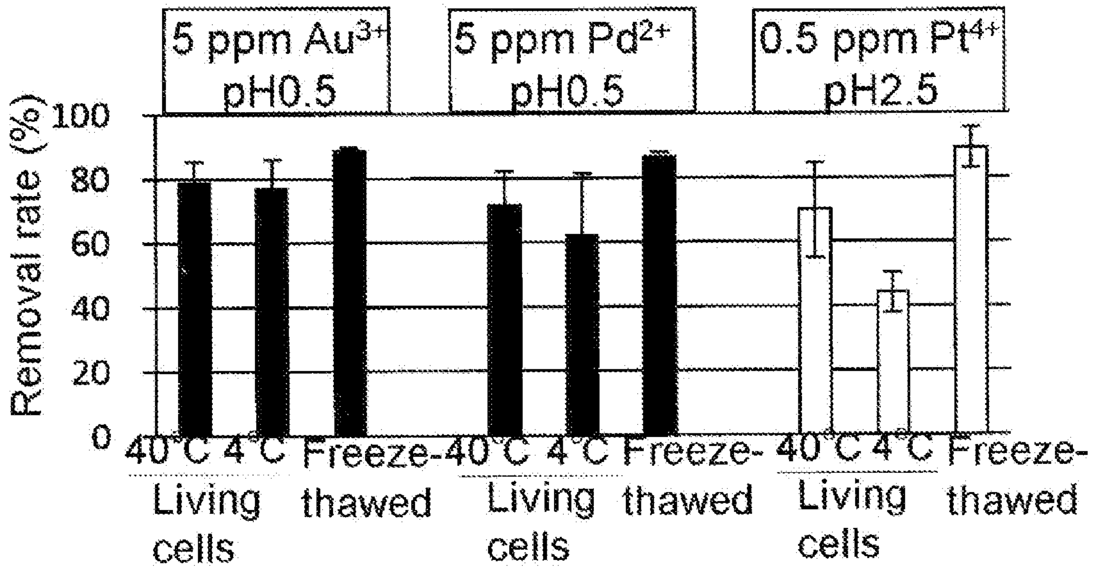
FIG. 10 is a diagram of a graph showing the recovery efficiencies of living cells (Living Cells) and dead cells (Freeze-thawed Cells) of *G. sulphuraria.*

Here, FIG. 10 is a diagram of graphs showing the recovery efficiency in living cells (Living Cells) and dead cells (Freeze-thawed Cells) of *G. sulphuraria*. As shown in the diagram, living cells or dead cells were cultured in a 0.4 M hydrochloric acid solution (pH 0.5) containing 5 ppm of $Au^{3+}$, a 0.4 M hydrochloric acid solution (pH 0.5) containing 5 ppm of $Pd^{2+}$, or a 40 mM hydrochloric acid solution (pH 2.5) containing 0.5 ppm of $Pt^{4+}$.

After culturing the cells at 40° C. or 4° C. for 30 minutes, a supernatant fraction was separated from the cells by centrifugation, and the concentrations were determined by ICP-MS. The percentage of each fraction was determined by subtracting the concentration obtainable as a control in the case of culturing without addition of cells from the concentration in each fraction. In addition, the concentrations of $Au^{3+}$, $Pd^{2+}$, and $Pt^{4+}$ without cell addition were 2.5±0.6, 4.6±0.7, and 0.4±0.2, respectively (each value was the average value of three independent experiment results for each metal±SD value).

As a result, as shown in FIG. 10, the recovery efficiency was higher with dead cells than with living cells. In addition, for palladium and platinum, when the culture temperature for living cells was decreased to 4° C., the recovery efficiency decreased. There was no change in the case of gold. In this regard, it is generally known that biosorption is not affected by temperature; however, this is speculated to be because palladium and platinum are known to undergo endothermic reactions (Wang, J., Wei, J., and Li, J., 2015. Rice straw modified by click reaction for selective extraction of noble metal ions. Bioresour. Technol. 177, 182-187).

Example 5

Subsequently, Example 5 relating to selective recovery in the presence of a plurality of metal ions will be described below.

A metal effluent dilution containing 70 ppm of iron, 360 ppm of copper, 5 ppm of platinum, 60 ppm of gold, 60 ppm of nickel, 6 ppm of tin, 18 ppm of palladium, and 12 ppm of zinc in aqua regia having an acid concentration of about 0.5 M was incubated for 30 minutes, with added cells of *G. sulphuraria* in an amount equivalent to 7 mg (+Cell), or without added cells (−Cell).

After culturing, the cells were caused to sediment by centrifugation, the concentrations of the respective metals in the supernatant were measured, and the removal rates were determined (following Table 2). The following table is a table showing the recovery efficiencies for $Au^{3+}$ and $Pd^{2+}$ from a metal effluent including a diluted aqua regia. Here, the aqua regia was produced from 57 ppm of $Fe^{2+/3+}$, 480 ppm $Cu^{2+}$, 4 ppm of $Pt^{4+}$, 53 ppm of $Au^{3+}$, 46 ppm of $Ni^{2+}$, 5 ppm of $Sn^{2+}$, 12 ppm of $Pd^{2+}$, 11 ppm of $Zn^{2+}$, and 0.56 M acid.

TABLE 2

| | $Fe^{2+/3+}$ (ppm) | $Cu^{2+}$ (ppm) | $Pt^{4+}$ (ppm) | $Au^{3+}$ (ppm) | $Ni^{2+}$ (ppm) | $Sn^{2+}$ (ppm) | $Pd^{2+}$ (ppm) | $Zn^{2+}$ (ppm) |
|---|---|---|---|---|---|---|---|---|
| −Cell | 88 ± 8.6 | 379 ± 46 | 5.8 ± 0.6 | 61 ± 9 | 59 ± 7.5 | 6.5 ± 0.8 | 18 ± 2.0 | 12 ± 1.4 |
| +Cell | 63 ± 11 | 358 ± 60 | 4.7 ± 0.7 | 5.9 ± 2.8 | 58 ± 9.4 | 5.5 ± 0.8 | 0.9 ± 0.2 | 12 ± 1.9 |
| Removal ratio | 8% | 6% | 19% | 90% | 0.30% | 16% | 95% | 6% |

As a result, only gold and palladium were recovered into the cells with high efficiency. Furthermore, gold and palladium could not be recovered in the aqua regia solution having a high acid concentration (following Table 3). The following table is a table showing the recovery efficiencies for $Au^{3+}$ and $Pd^{2+}$ from a metal effluent including an aqua regia having high acidity. Here, the aqua regia was produced from 570 ppm of $Fe^{2+/3+}$, 4800 ppm of $Cu^{2+}$, 40 ppm of $Pt^{4+}$, 530 ppm of $Au^{3+}$, 460 ppm of $Ni^{2+}$, 50 ppm of $Sn^{2+}$, 120 ppm of $Pd^{2+}$, 110 ppm of $Zn^{2+}$, and 5.6 M acid.

TABLE 3

| | Elements | | | | | | | |
|---|---|---|---|---|---|---|---|---|
| Sample | $Fe^{2+/3+}$ ppm | $Cu^{2+}$ ppm | $Pt^{4+}$ ppm | $Au^{3+}$ ppm | $Ni^{2+}$ ppm | $Sn^{2+}$ ppm | $Pd^{2+}$ ppm | $Zn^{2+}$ ppm |
| −Cell | 529 ± 24 | 3364 ± 304 | 42 ± 15 | 464 ± 25 | 476 ± 39 | 40.2 ± 7.8 | 135 ± 10 | 182 ± 40 |
| +Cell | 475 ± 28 | 3237 ± 235 | 26 ± 2.3 | 406 ± 69 | 428 ± 9.6 | 27.8 ± 2.0 | 116 ± 6.3 | 161 ± 13 |
| (Removal rate %) | (10%) | (3.8%) | (3.8%) | (13%) | (10%) | (31%) | (14%) | (12%) |

Furthermore, even when the gold concentration was about 580 ppm, a recovery efficiency of 60% was maintained (following Table 4). The following table is a table showing the recovery efficiencies achieved by *G. sulphuraria* cells from a metal effluent including an aqua regia containing $Au^{3+}$ at a high concentration. Here, the aqua regia was produced from 70 ppm of $Fe^{2+/3+}$, 120 ppm of $Cu^{2+}$, 3 ppm of $Pt^{4+}$, 577 ppm of $Au^{3+}$, 210 ppm of $Ni^{2+}$, 14 ppm of $Sn^{2+}$, and 0.43 M acid.

TABLE 4

| | $Fe^{2+/3+}$ (ppm) | $Cu^{2+}$ (ppm) | $Pt^{4+}$ (ppm) | $Au^{3+}$ (ppm) | $Ni^{2+}$ (ppm) | $Sn^{2+}$ (ppm) |
|---|---|---|---|---|---|---|
| −Cell | 86 ± 14 | 107 ± 44 | 4.5 ± 0.6 | 580 ± 57 | 262 ± 48 | 24 ± 3.5 |
| +Cell | 63 ± 7.6 | 73 ± 11 | 3.7 ± 0.3 | 199 ± 72 | 223 ± 19 | 18 ± 1.3 |
| Removal rate | 26% | 28% | 17% | 66% | 14% | 23% |

As a result of the above, it was confirmed that even in a case in which a plurality of metal ions exist in large quantities, only noble metal ions can be selectively recovered.

Example 6

Example 6 relating to the elution of the noble metal ions recovered into an algal body will be described below.

Similarly to Example 5 described above, a metal effluent dilution containing 70 ppm of iron, 360 ppm of copper, 5 ppm of platinum, 60 ppm of gold, 60 ppm of nickel, 6 ppm of tin, 18 ppm of palladium, and 12 ppm of zinc in an aqua regia having an acid concentration of about 0.5 M was incubated for 15 minutes with added cells of *G. sulphuraria* in an amount equivalent to 7 mg.

Then, the cells that had recovered 57 ppm of gold and 15 ppm of palladium were incubated for 30 minutes in an elution solution indicated in the following Table 5. The following Table 5 is a table showing the elution of $Au^{3+}$ and $Pd^{2+}$ from the *G. sulphuraria* cells that had recovered 59±7 ppm of $Au^{3+}$ and 15±1 ppm of $Pd^{2+}$ from a diluted metal effluent. Regarding the cells, cells that had been incubated for 15 minutes in a diluted metal effluent containing 57 ppm of $Fe^{2+}/^{3+}$, 480 ppm of $Cu^{2+}$, 4 ppm of $Pt^{4+}$, 53 ppm of $Au^{3+}$, 46 ppm of $Ni^{2+}$, 5 ppm of $Sn^{2+}$, 12 ppm of $Pd^{2+}$, 11 ppm of $Zn^{2+}$, and 0.56 M acid were used (each value represents the average value±S.E. value).

TABLE 5

| Elution solution | $Au^{3+}$ ppm | $Pd^{2+}$ ppm | $Fe^{2+/3+}$ ppm | $Cu^{2+}$ ppm | $Pt^{4+}$ ppm | $Ni^{2+}$ ppm | $Sn^{2+}$ ppm | $Zn^{2+}$ ppm |
|---|---|---|---|---|---|---|---|---|
| 0.4M HCl | 2.4 ± 0.8 | 0.0 ± 0.0 | 2.2 ± 2.2 | 11.6 ± 0.1 | ND | ND | 0.2 ± 0.0 | ND |
| 0.2M $NH_4Br$, 2.8% $NH_3$ (pH 11) | 29.2 ± 2.3 | 11.6 ± 0.7 | ND | 3.8 ± 3.8 | ND | ND | ND | ND |
| 0.2M $NH_4Cl$, 2.8% $NH_3$ (pH 11) | 28.2 ± 0.3 | 11.3 ± 0.3 | ND | ND | ND | ND | ND | ND |
| 0.1M KOH | 3.9 ± 1.6 | 0.4 ± 0.1 | ND | 3.8 ± 3.8 | ND | ND | 0.4 ± 0.1 | ND |
| 1M Thiourea, 0.1M HCl | 46.2 ± 6.4 | 13.4 ± 1.2 | 5.5 ± 2.8 | 11.6 ± 0.1 | 0.6 ± 0.0 | ND | ND | ND |

As a result, 48% of gold ions and 70% of palladium ions were eluted into the solution. Incorporation of iron or copper was significantly suppressed compared to the existing methods of utilizing thiourea (above Table 5). Furthermore, it was found that the recovery efficiency significantly decreases when ammonia only is used, or ammonium ions only are used (following Table 6). The following table is a table showing the various metal concentrations and recovery rates in an elution solution in which the cells that had recovered $Au^{3+}$ and $Pd^{2+}$ were incubated for 30 minutes.

TABLE 6

| Concentration of $Au^{3+}$ and $Pd^{2+}$ retained by the cells before the elution | Elution solution | Concentration and recovery rate in the elution solution after the elution: $Au^{3+}$ ppm | $Pd^{2+}$ ppm | $Au^{3+}$ % | $Pd^{2+}$ % |
|---|---|---|---|---|---|
| 121 ppm $Au^{3+}$, 36 ppm $Pd^{2+}$ | HCl (pH 0.5) | 3.3 ± 2.9 | 0 ± 0 | 2.7 | 0 |
| 121 ppm $Au^{3+}$, 36 ppm $Pd^{2+}$ | 2.8% $NH_3$ | 7.6 ± 0.3 | 2.7 ± 0.3 | 6.2 | 7.7 |
| 121 ppm $Au^{3+}$, 36 ppm $Pd^{2+}$ | 14% $NH_3$ | 11 ± 1.3 | 3.6 ± 0.6 | 9 | 10.2 |
| 65 ppm $Au^{3+}$, 18 ppm $Pd^{2+}$ | 0.2M $NH_4Cl$ (pH 3) | 5.6 ± 0.2 | 0 ± 0 | 8.7 | 0 |
| 65 ppm $Au^{3+}$, 18 ppm $Pd^{2+}$ | 0.2M $NH_4Cl$ (pH 7) | 12 ± 2.1 | 2.4 ± 0.2 | 18 | 13 |
| 65 ppm $Au^{3+}$, 18 ppm $Pd^{2+}$ | 0.2M $NH_4Cl$ (pH 11) | 26 ± 0.8 | 8.9 ± 0.5 | 39 | 49 |

As disclosed in this Example 6, it was confirmed that the recovery into the algal body was achieved within 15 minutes, the extraction from the algal body was achieved within 30 minutes, and treatment can be achieved in a short time period. Furthermore, it was confirmed by this Example 6 that noble metals can be selectively recovered from an aqua regia solution using an alga belonging to the order Cyanidiales by adjusting the acid concentration of the solution to be about 0.5 M. Furthermore, it was found that a noble metal can be extracted and purified as a complex by utilizing a mixed liquid of aqueous ammonia and an ammonium salt (ammonium chloride, ammonium sulfate, ammonium carbonate, ammonium bromide, or the like).

From this, it was confirmed that compared to a method of utilizing thiourea under acidic conditions, incorporation of other metals can be suppressed, and purity can be increased. It was confirmed that since complexes that are also used for solvent extraction of noble metals are used for elution and purification of noble metals, application of the method to conventional chemical processes or production processes is facilitated, and the method is superior to conventional methods from the viewpoint of economic efficiency or from an environmental viewpoint.

Here, the experimental results obtained in the case of using chlorella instead of red alga *G. sulphuraria* as a control experiment are shown in the following Table 7. The following table is a table showing the recovery efficiencies for $Au^{3+}$ and $Pd^{2+}$ from a metal effluent including a diluted aqua regia using chlorella cells. Meanwhile, the aqua regia was produced from 57 ppm of $Fe^{2+}/^{3+}$, 480 pm of $Cu^{2+}$, 4 ppm of $Pt^{4+}$, 53 ppm of $Au^{3+}$, 46 ppm of $Ni^{2+}$, 5 ppm of $Sn^{2+}$, 12 ppm of $Pd^{2+}$, 11 ppm of $Zn^{2+}$, and 0.56 M acid (each value is the average value±S.D. value).

TABLE 7

| | $Fe^{2+/3+}$ (ppm) | $Cu^{2+}$ (ppm) | $Pt^{4+}$ (ppm) | $Au^{3+}$ (ppm) | $Ni^{2+}$ (ppm) | $Sn^{2+}$ (ppm) | $Pd^{2+}$ (ppm) | $Zn^{2+}$ (ppm) |
|---|---|---|---|---|---|---|---|---|
| −Cell | 52 ± 13 | 314 ± 130 | 48 ± 0.6 | 69 ± 9 | 44 ± 84 | 5.7 ± 0.8 | 16.2 ± 2.4 | 15 ± 7 |
| +Cell | 64 ± 17 | 339 ± 60 | 49 ± 1.0 | 41 ± 17 | 47 ± 15 | 5.6 ± 1.1 | 3.4 ± 1.4 | 19 ± 12 |
| Removal rate | — | — | — | 40% | — | 2% | 79% | — |

Since aqua regia has very high metal solubility, even in the case of chlorella that has been reported to recover gold ions with high efficiency in a hydrochloric acid solution, the recovery efficiency for gold ions and palladium ions from an aqua regia solution are 40% and 79%, respectively as shown in the above table, while in the present method, the recovery efficiencies are 90% or higher (Table 7 described above). Here, the following Table 8 is a table showing the recovery rates from a metal effluent including an aqua regia containing $Au^{3+}$ at a high concentration. In addition, the cells were incubated for 15 minutes in a diluted metal effluent containing 57 ppm of $Fe^{2+}/^{3+}$, 480 ppm of $Cu^{2+}$, 4 ppm of $Pt^{4+}$, 53 ppm of $Au^{3+}$, 46 ppm of $Ni^{2+}$, 5 ppm of $Sn^{2+}$, 12 ppm of $Pd^{2+}$, 11 ppm of $Zn^{2+}$, and 0.56 M acid (each value is the average value±S.E. value).

TABLE 8

| Elution solution | $Au^{3+}$ ppm | $Pd^{2+}$ ppm | $Fe^{2+/3+}$ ppm | $Cu^{2+}$ ppm | $Pt^{4+}$ ppm | $Ni^{2+}$ ppm | $Sn^{2+}$ ppm | $Zn^{2+}$ ppm |
|---|---|---|---|---|---|---|---|---|
| 0.4M HCl | 4.6 ± 1.4 | 0.2 ± 0.1 | ND | 3.8 ± 3.8 | ND | ND | 0.1 ± 0.1 | ND |
| 0.2M $NH_4Cl$, 2.8% $NH_3$ (pH 11) | 8.7 ± 1.3 | 8.2 ± 0.1 | ND | 7.5 ± 3.8 | ND | ND | ND | ND |
| 1M Thiourea, 0.1M HCl | 11.9 ± 4.2 | 10.0 ± 0.7 | 2.6 ± 2.6 | 3.8 ± 3.8 | 0.1 ± 0.0 | ND | ND | ND |

Example 7

Subsequently, Example 7 relating to recovery and nanoparticulation by reduction of gold ions at a low concentration by *G. sulphuraria* will be described below.

Figure 11:
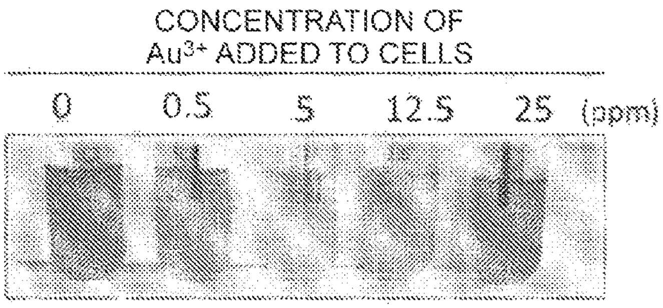
FIG. 11 is a diagram (photograph as a substitute of a diagram) showing the gold ion concentrations added to cells and the color changes of culture fluids.

First, gold ions at a concentration of 0 to 25 ppm were added to cells of *G. sulphuraria*. FIG. 11 is a diagram (photograph as a substitute for a diagram) showing the concentration of gold ions added to the cells and the color changes in the culture fluid. As a result, *G. sulphuraria* recovered 25 ppm or less of gold ions with an efficiency of 90% or higher. The following Table 9 is a table showing the concentration of gold ions added to the cells and the recovery rate (%) into the cells.

TABLE 9

| Concentration of $Au^{3+}$ added to cells (ppm) | $Au^{3+}$ concentration in supernatant after 30 minutes of addition (ppm) −Cell | +Cell | Recovery efficiency (%) |
|---|---|---|---|
| 0 | 0.03 ± 0.004 | 0.03 ± 0.008 | — |
| 0.5 | 0.37 ± 0.008 | 0.03 ± 0.004 | 91.9 |
| 5 | 4.01 ± 0.134 | 0.03 ± 0.003 | 99.3 |
| 12.5 | 13.1 ± 0.55 | 0.04 ± 0.011 | 99.7 |
| 25 | 26.3 ± 0.08 | 0.07 ± 0.014 | 99.8 |

Figure 12:
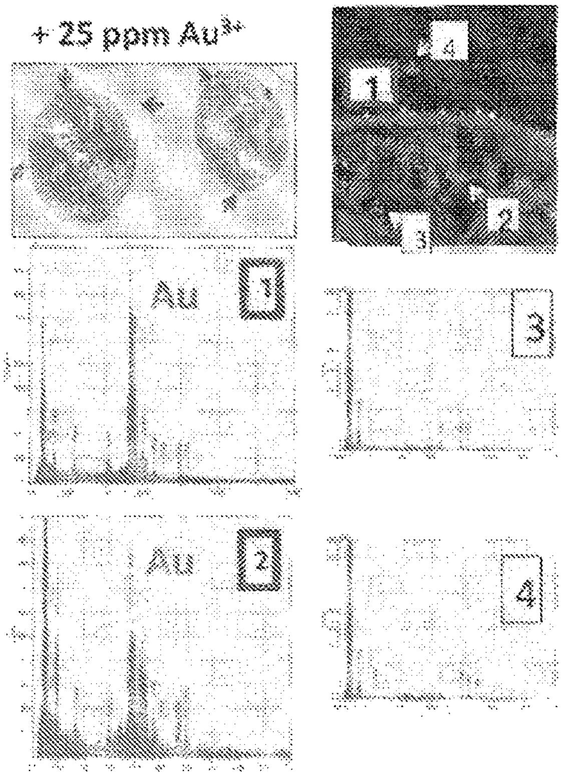
FIG. 12 is a diagram (photographs as substitutes of diagrams) showing the positions of gold nanoparticles in a microscopic image of cells and the results for an Au composition analysis by TEM-EDS.

Furthermore, it was found that at 25 ppm, the cells of *G. sulphuraria* not only recover gold ions but also reduce the gold ions thus recovered, and form reddish purple gold nanoparticles mainly in the cell surface layer. Here, FIG. 12 is a diagram (photographs as a substitute for diagrams) showing the positions of gold nanoparticles in a microscopic image of cells and the Au composition analysis results obtained by TEM-EDS.

Figure 13:
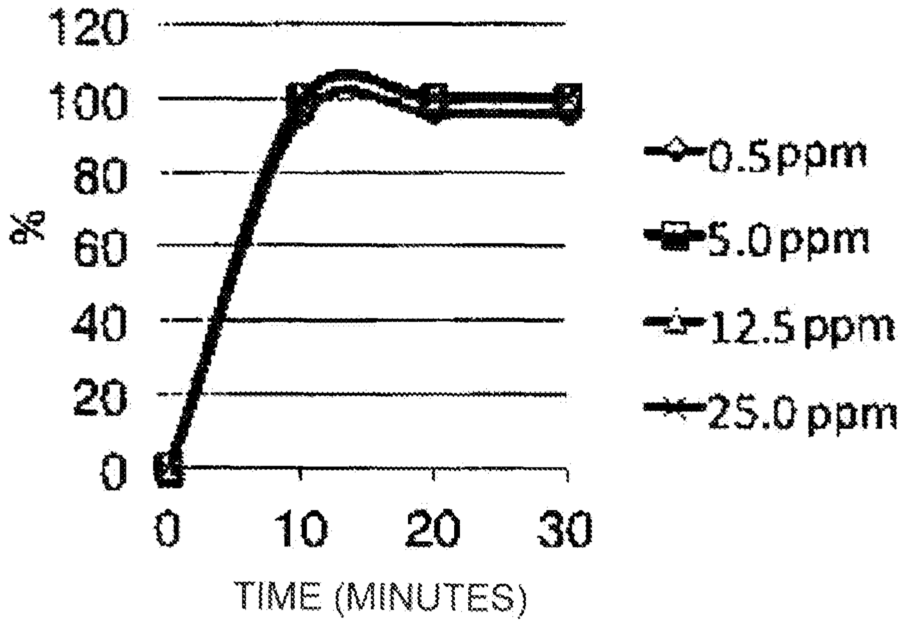
FIG. 13 is a diagram of a graph showing the recovery rates at gold ion concentrations of 0.5 to 25.0 ppm and incubation times.
Figure 14:
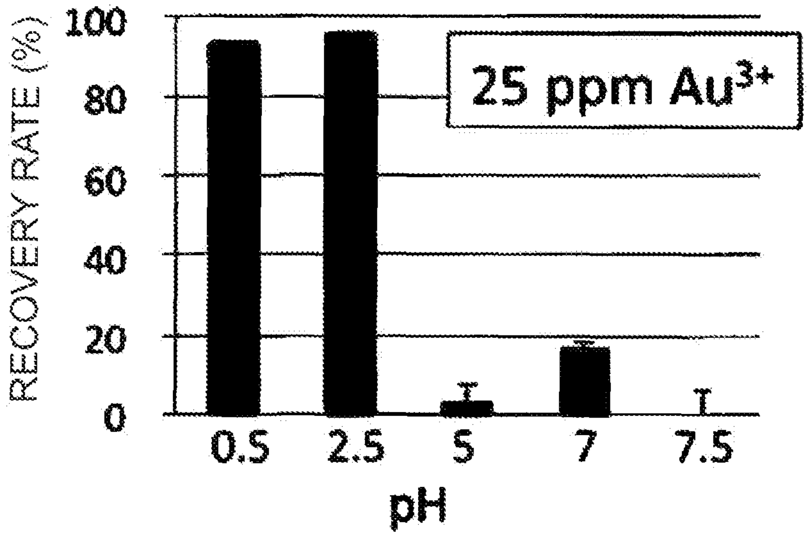
FIG. 14 is a diagram of a graph showing the pH-dependent recovery rates for gold ions into cells.

Furthermore, FIG. 13 is a diagram of a graph showing the recovery rates at a gold ion concentration of 0.5 to 25.0 ppm and the incubation time. As shown in FIG. 13, the recovery of gold ions reached 100% within 10 minutes. Furthermore, this recovery of gold ions occurred under acidic conditions. Here, FIG. 14 is a diagram of a graph showing pH-dependent recovery rates of gold ions into cells.

Figure 15:
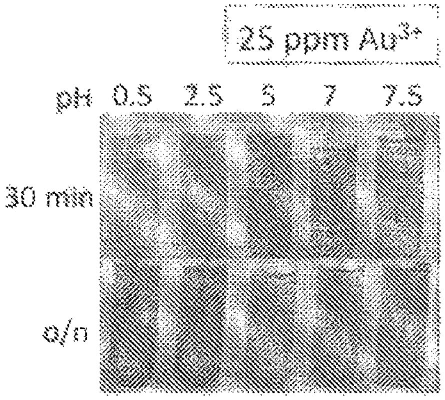
FIG. 15 is a diagram (photograph as a substitute for a diagram) showing color changes of culture fluids depending on pH and the incubation time.

Furthermore, here, FIG. 15 is a diagram (photograph as a substitute for a diagram) showing the color changes in the culture fluid depending on pH and the incubation time. As shown in FIG. 15, at the time point of 30 minutes where the recovery of gold ions reached 100%, the color of the culture fluid was yellow, and the color changed to reddish purple after incubation overnight (o/n: over night).

Figure 24:
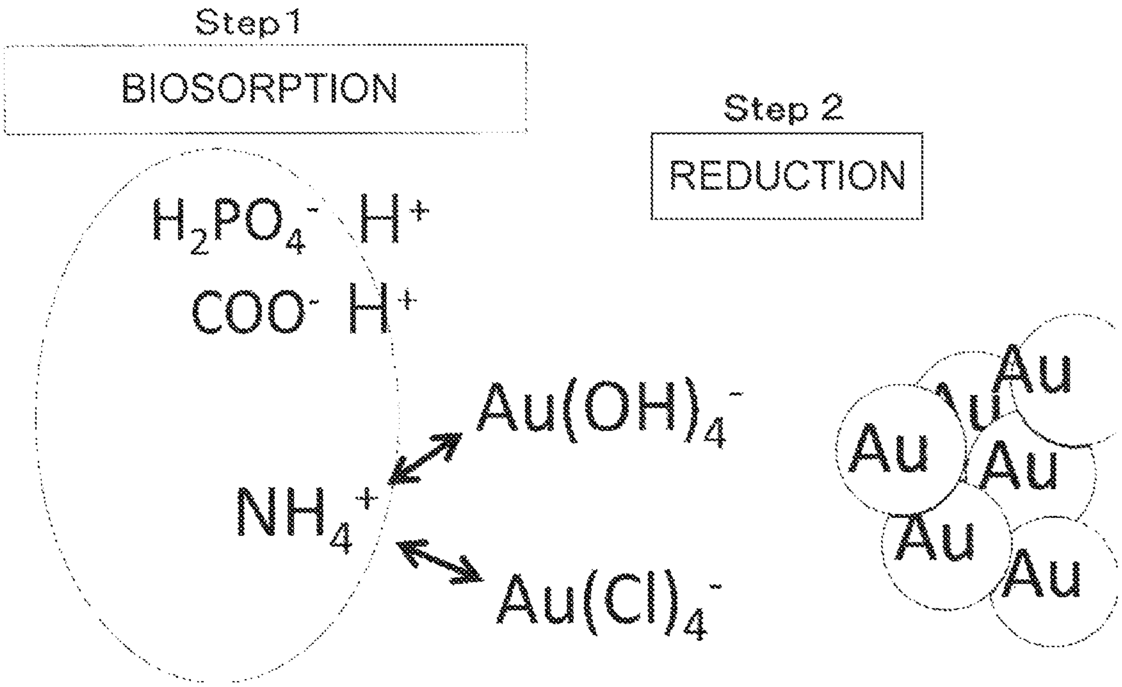
FIG. 24 is a diagram schematically illustrating a first stage of biosorption (adsorption) and a second stage of reduction.

According to these results, it was found that reduction and recovery of gold ions by *G. sulphuraria* involve two steps of a rapid recovery step that takes 10 minutes or less (recovery process) and a reduction step that requires several hours (reduction process) (see FIG. 24). In the former recovery step, the recovery of gold ions into a cell surface layer is based on biosorption (see Examples 3 to 6 described above). Here, FIG. 16 is a diagram (photograph as a substitute for a diagram) showing the color changes in the culture fluid occurring in a case in which incubation was performed at various temperatures in a dark place and a bright place.

Figure 16:
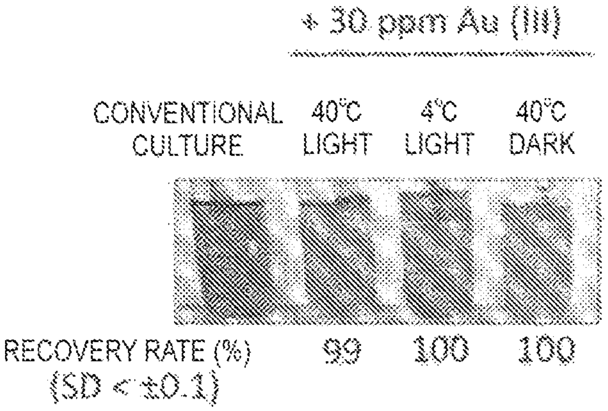
FIG. 16 is a diagram (photograph as a substitute for a diagram) showing color changes of culture fluids in the case of performing incubation at various temperatures in a dark place and a bright place.

As shown in FIG. 16, it was found that in the recovery step, light and temperature do not have any influence; however, in the reduction step, reduction of gold ions requires light and temperature.

Example 8

Example 8 relating to photoreduction of gold ions by porphyrins (pheophytin and coproporphyrin) will be described below.

Subsequently, based on the clue that reduction of gold ions depends on light and temperature, an investigation was conducted on the substance related to the reduction of gold ions in the latter reduction step. Here, FIG. 17 is a flow chart showing the method for preparing various cell fractions.

Figure 17:
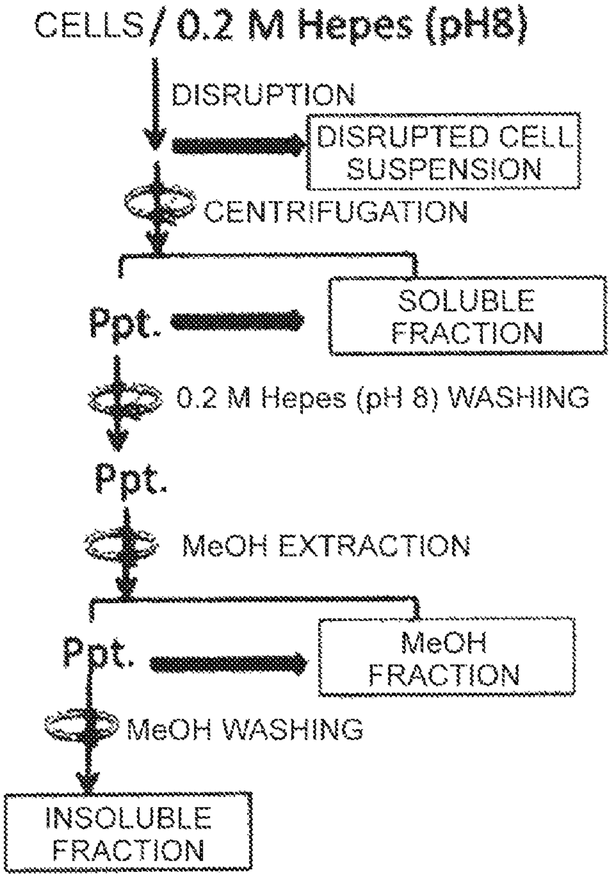
FIG. 17 is a flow chart showing a method for producing various cell fractions.
Figure 18:
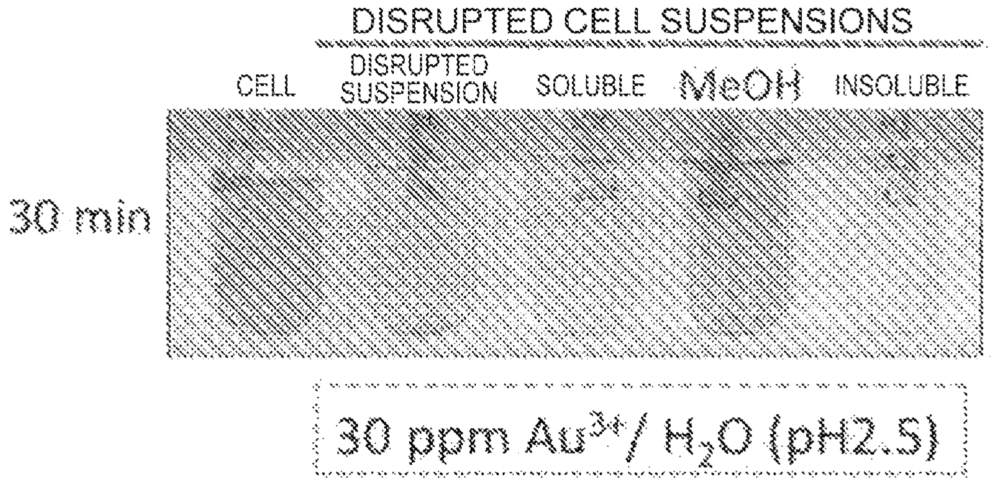
FIG. 18 is a diagram (photograph as a substitute for a diagram) showing color changes obtained after adding gold ions to various cell fractions and culturing the cell fractions for 30 minutes.

As shown in FIG. 17, cells were fractionated, gold ions were added to various fractions, and incubation was performed for 30 minutes. Here, FIG. 18 is a diagram (photograph as a substitute for a diagram) showing color changes occurring after adding gold ions to various cell fractions and culturing the cells for 30 minutes. As shown in FIG. 18, after the incubation, reduction of gold ions occurred in a methanol (MeOH)-extracted fraction, and gold nanoparticles were observed.

Next, the pH was changed, and incubation of the MeOH-extracted fraction and gold ions was performed. Here, FIG. 19 is a diagram (photograph as a substitute for a diagram) showing the results obtained by incubating the methanol-extracted fraction by changing the pH.

Figure 19:
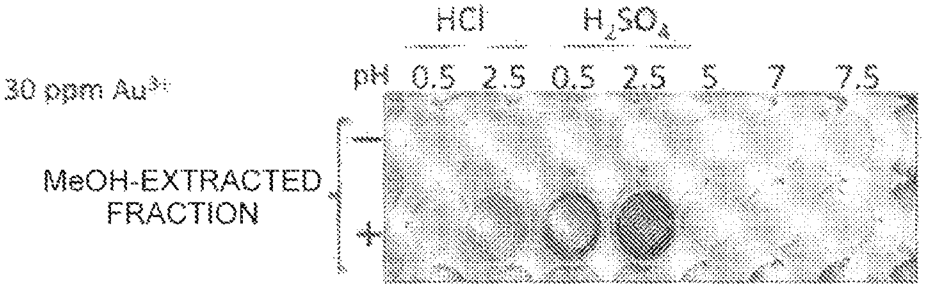
FIG. 19 is a diagram (photograph as a substitute for a diagram) showing the results obtained by incubating a methanol-extracted fraction by varying the pH.
Figure 20:
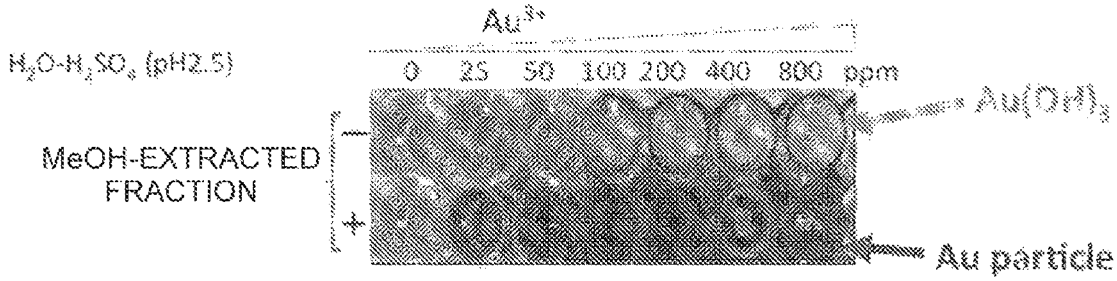
FIG. 20 is a diagram (photograph as a substitute for a diagram) showing the results obtained by incubating a methanol-extracted fraction by varying the gold ion concentration.

As shown in FIG. 19, reduction of gold ions occurred only under acidic conditions. Thus, the gold ion concentration was increased, and incubation was performed. FIG. 20 is a diagram (photograph as a substitute for a diagram) showing the results of incubating the methanol-extracted fraction while changing the gold ion concentration. As shown in FIG. 20, gold-colored structures having a size larger than reddish purple gold nanoparticles were observed along with an increase in the concentration of gold ions. In addition, in the control (upper row in FIG. 20: MeOH-extracted fraction-) in which the MeOH-extracted fraction was not added and methanol and gold ions were simply mixed, a yellowish brown precipitate, which was considered to be gold hydroxide, was observed.

Figure 21:
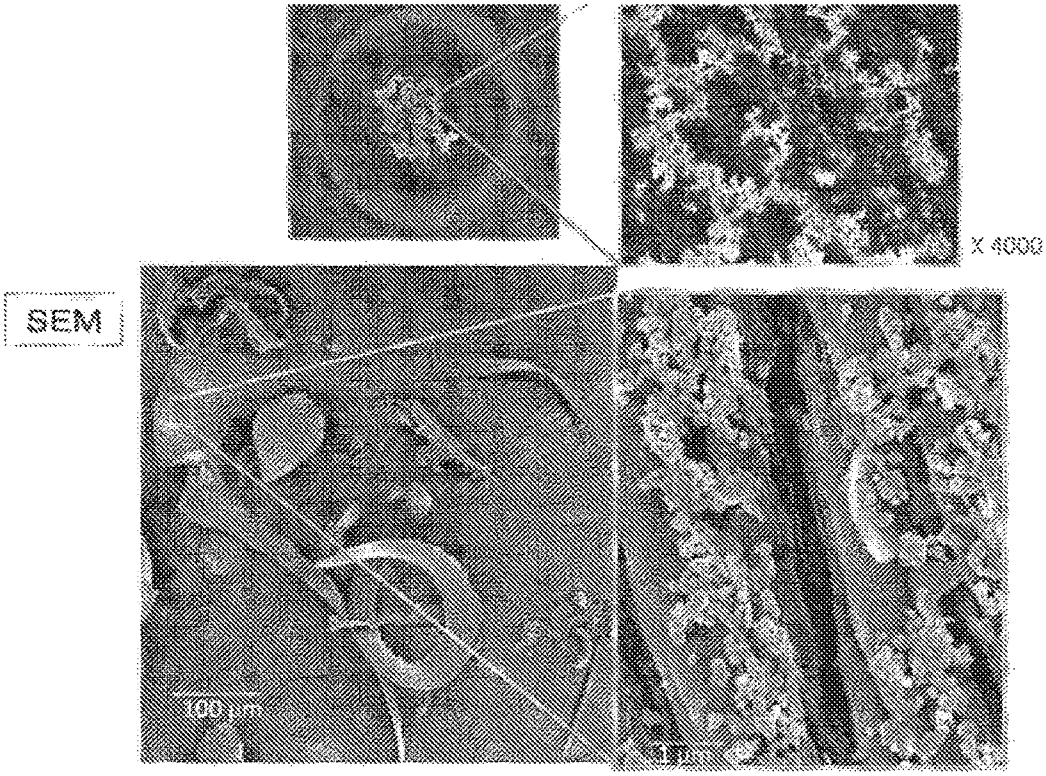
FIG. 21 is a diagram (photographs as a substitute for a diagram) showing CCD camera images and SEM images of a MeOH-extracted fraction and gold-colored structures produced by incubation of gold ions at a high concentration.

Subsequently, the gold-colored structures produced by incubation of the MeOH-extracted fraction and gold ions at a high concentration were observed with a CCD camera and a SEM. FIG. 21 is a diagram (photographs as a substitute for diagrams) showing CCD camera images and SEM images of the gold-colored structures produced by incubation of the MeOH-extracted fraction and gold ions at a high concentration.

As shown in FIG. 21, ribbon-shaped structures were observed, and it was found that the surface thereof was covered with fine particles that were considered to be gold particles. As described above in connection with FIG. 2 and FIG. 5, *G. sulphuraria* releases coproporphyrin out of the cell. Furthermore, chlorophyll that exists in a large quantity in the cell and is extracted with MeOH is such that under acidic conditions, magnesium as the central metal comes off, and the resultant exists as pheophytin. Furthermore, photoreduction of $Fe^{3+}$ to $Fe^{2+}$ by porphyrin in methanol is known (Bartocci et al., 1980, J. Am. Chem. Soc., 102, 7067-7072).

Figure 22:
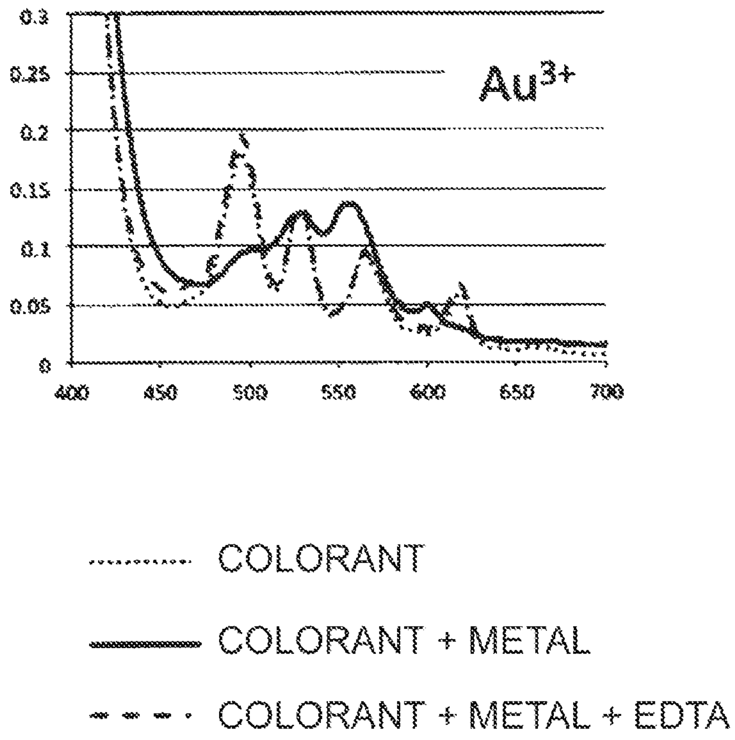
FIG. 22 is a diagram of a graph showing spectral shifts at the visible light portion obtained in a case in which gold ions were added to coproporphyrin.

Here, FIG. 22 is a diagram of a graph showing spectral shifts at the visible light portion obtained in a case in which gold ions were added to coproporphyrin. As shown in FIG. 22, when gold ions are added to coproporphyrin that has been purified from the outside of the cells of *G. sulphuraria*, spectral shifts occur at the visible light portion, and coproporphyrin chelates gold ions.

Figure 23:
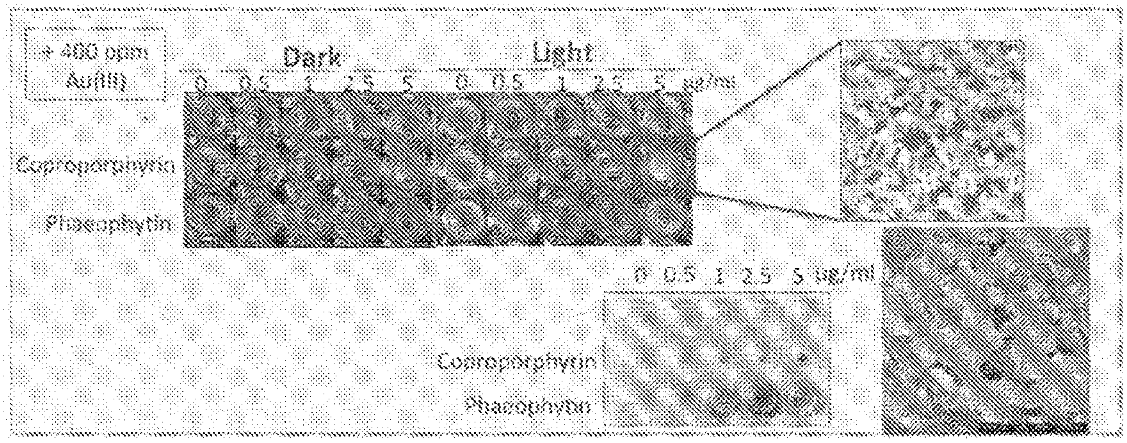
FIG. 23 is a diagram (photographs as a substitute for a diagram) showing the results obtained by adding gold ions to preparations of coproporphyrin and pheophytin and incubating the preparations overnight.

Here, FIG. 23 is a diagram (photographs as a substitute for diagrams) showing the results of adding gold ions to preparations of coproporphyrin and pheophytin and incubating the preparations overnight. As shown in FIG. 23, it was found that when light is radiated in the presence of coproporphyrin or pheophytin, reduction of gold ions and formation of gold particles are promoted.

Photoreduction of gold ions by porphyrins occurred with about 50 μE of light, and strong light such as laser light was not needed. From these results, it was found that nanoparticulation of gold ions by photoreduction by porphyrins such as coproporphyrin and pheophytin occurs, and gold nanoparticles having different sizes are formed as a result of the difference in the type of porphyrin.

Based on these findings, when porphyrins are used, recovery and purification of gold ions with high purity can now be carried out by nanoparticulation by reduction of gold ions at concentrations lower than conventional cases. Furthermore, it was found that since porphyrins have selectivity, even under conditions in which a plurality of metal ions exist in large quantities, only gold ions can be selectively purified as gold particles with high purity.

Example 9

Here, Example 9 of comparing a material derived from an alga belonging to the order Cyanidiales and chlorella will be described below.

As a result of an experiment, a cell surface layer of an alga belonging to the order Cyanidiales exhibited superior adsorption and desorption of gold (metal), compared to a surface layer of algae of the prior art technologies concerning bioleaching and biosorption using chlorella (for example, Japanese Examined Patent Publication No. S62-500931) (see the following Table 10). Furthermore, it was found, based on the Examples described above, that unlike the priority art technologies related to red algae (Japanese Unexamined Patent Publication No. 2013-67826), the function is achieved even with dead cells or a cell surface layer only. Thereby, it was confirmed that a cell surface layer or an artificial material simulating a cell surface layer can be processed into or supplied to a form that can be more easily utilized as a material derived from an alga belonging to the order Cyanidiales.

TABLE 10

Table Comparison of recovery efficiencies for gold ions from metal effluent, obtained by utilizing Galdieria and Chlorella

| | Galdieria (ppm) | Chlorella (ppm) |
|---|---|---|
| −Cell | 61 ± 9 | 69 ± 9 |
| +Cell | 5.9 ± 2.8 | 41 ± 17 |
| Removal rate | 90% | 40% |

INDUSTRIAL APPLICABILITY

According to the present invention, an agent for selective metal recovery, a metal recovery method, and a metal elution method, by which selective recovery, elution, purification and the like of metals can be efficiently carried out at low cost, can be provided. Therefore, the present invention is highly valuable for industrial utilization in recycling of noble metals or rare metals, such as the separation of rare earth elements from metal effluent containing iron and reduction and recovery of gold ions, recovery of noble metals or rare metals included at low concentrations in the environment, elution or purification of noble metal ion complexes from living organisms or adsorbent materials, and the like.

The invention claimed is:

1. A method of recovering gold or palladium, the method comprising:

adding a material to a noble metal solution containing gold or palladium, wherein the material comprises freeze-thawed dead cells of algae belonging to *Galdieria sulphuraria*, wherein the material does not contain living cells of the algae;

adsorbing noble metal ions from the noble metal solution to the material at a pH of about 5;

optionally, reducing the noble metal ions to form nanoparticles; and recovering the nanoparticles and/or the material with adsorbed noble metal ions from the noble metal solution, wherein the method improves recovery of the noble metal when compared to using living cells, and wherein the adsorbing comprises adsorbing at least 4 ppm of gold ion from the noble metal solution, or at least 4 ppm of palladium ion.

2. The metal recovery method according to claim 1, wherein the material further comprises a porphyrin, and the porphyrin comprises coproporphyrin.

3. The metal recovery method according to claim 1, wherein the material further comprises a porphyrin, and the porphyrin comprises a protonated compound.

4. The metal recovery method according to claim 1, wherein the material comprises the algae's cell surface layer, and the adsorbing comprises adsorbing a noble metal ion complex by an electrostatic interaction or ion exchange.

5. The metal recovery method according to claim 1, wherein the material further comprises a porphyrin, and the porphyrin forms the nanoparticles by reducing a noble metal.

6. The metal recovery method according to claim 1, comprising forming the nanoparticles by reducing a noble metal ion.

7. The metal recovery method according to claim 1, wherein the material further comprises porphyrin.

8. The metal recovery method according to claim 1, wherein the material further comprises a cell surface layer of the algae.

* * * * *